United States Patent
Fischer et al.

(10) Patent No.: US 9,572,342 B2
(45) Date of Patent: Feb. 21, 2017

(54) USE OF AN ANTHRANILIC DIAMIDE DERIVATIVES WITH HETEROAROMATIC AND HETEROCYCLIC SUBSTITUENTS IN COMBINATION WITH A BIOLOGICALCONTROL AGENT

(71) Applicant: BAYER INTELLECTUAL PROPERTY GMBH, Monheim (DE)

(72) Inventors: Rüdiger Fischer, Pulheim (DE); Heiki Hungenberg, Langenfeld (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 43 days.

(21) Appl. No.: 14/366,110

(22) PCT Filed: Dec. 17, 2012

(86) PCT No.: PCT/EP2012/075840
§ 371 (c)(1),
(2) Date: Jun. 17, 2014

(87) PCT Pub. No.: WO2013/092516
PCT Pub. Date: Jun. 27, 2013

(65) Prior Publication Data
US 2014/0364458 A1    Dec. 11, 2014

(30) Foreign Application Priority Data
Dec. 19, 2011   (EP) ..................................... 11194336

(51) Int. Cl.
A01N 43/713       (2006.01)
(52) U.S. Cl.
CPC .................................. A01N 43/713 (2013.01)
(58) Field of Classification Search
None
See application file for complete search history.

(56) References Cited

U.S. PATENT DOCUMENTS

| | | | |
|---|---|---|---|
| 8,324,390 B2 * | 12/2012 | Fischer | A01N 43/713 546/275.4 |
| 8,536,092 B2 * | 9/2013 | Alig | A01N 43/56 504/100 |
| 8,946,236 B2 * | 2/2015 | Alig | A01N 43/56 514/256 |
| 2010/0029478 A1 | 2/2010 | Alig et al. | |
| 2010/0292226 A1 | 11/2010 | Funke et al. | |
| 2011/0311503 A1 | 12/2011 | Funke et al. | |
| 2012/0010249 A1 | 1/2012 | Fischer et al. | |
| 2013/0324560 A1 | 12/2013 | Alig et al. | |

FOREIGN PATENT DOCUMENTS

| | | |
|---|---|---|
| WO | 0170671 A2 | 9/2001 |
| WO | 03015518 A1 | 2/2003 |
| WO | 03015519 A1 | 2/2003 |
| WO | 03016282 A2 | 2/2003 |
| WO | 03016283 A1 | 2/2003 |
| WO | 03016284 A1 | 2/2003 |
| WO | 03024222 A1 | 3/2003 |
| WO | 03027099 A1 | 4/2003 |
| WO | 03062226 A1 | 7/2003 |
| WO | 04027042 A2 | 4/2004 |
| WO | 04033468 A1 | 4/2004 |
| WO | 2004046129 A1 | 6/2004 |
| WO | 2004067528 A1 | 8/2004 |
| WO | 2005077934 A1 | 8/2005 |
| WO | 2005085234 A2 | 9/2005 |
| WO | 2005118552 A1 | 12/2005 |
| WO | 2006000336 A2 | 1/2006 |
| WO | 2006023783 A1 | 3/2006 |
| WO | 2006040113 A1 | 4/2006 |
| WO | 2006111341 A1 | 10/2006 |
| WO | 2007006670 A1 | 1/2007 |
| WO | 2007020877 A1 | 2/2007 |
| WO | 2007024833 A1 | 3/2007 |
| WO | 2011157778 A1 | 12/2011 |

OTHER PUBLICATIONS

International Search Report received in PCT/EP2012/075840, mailed Jan. 30, 2013.

* cited by examiner

*Primary Examiner* — Kamal Saeed
(74) *Attorney, Agent, or Firm* — McBee Moore Woodward Vanik, IP LLC

(57) ABSTRACT

A composition comprising a compound of formula (I):

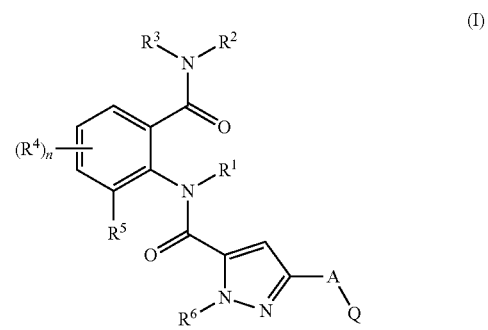

in which $R^1$, $R^2$, $R^3$, $R^4$, $R^5$, $R^6$, A, Q and n can have the definitions stated in the description, and at least one biological control agent selected from bacteria, fungi or yeasts, protozoas, viruses, entomopathogenic nematodes, and botanical extracts, or products produced by microorganisms including proteins or secondary metabolites, and optionally an inoculant, for reducing overall damage of plants and plant parts as well as losses in harvested fruits or vegetables caused by insects, nematodes and phytopathogens.

21 Claims, 1 Drawing Sheet

Genealogy of Group 1 bacteria according to Ash et al., 1991
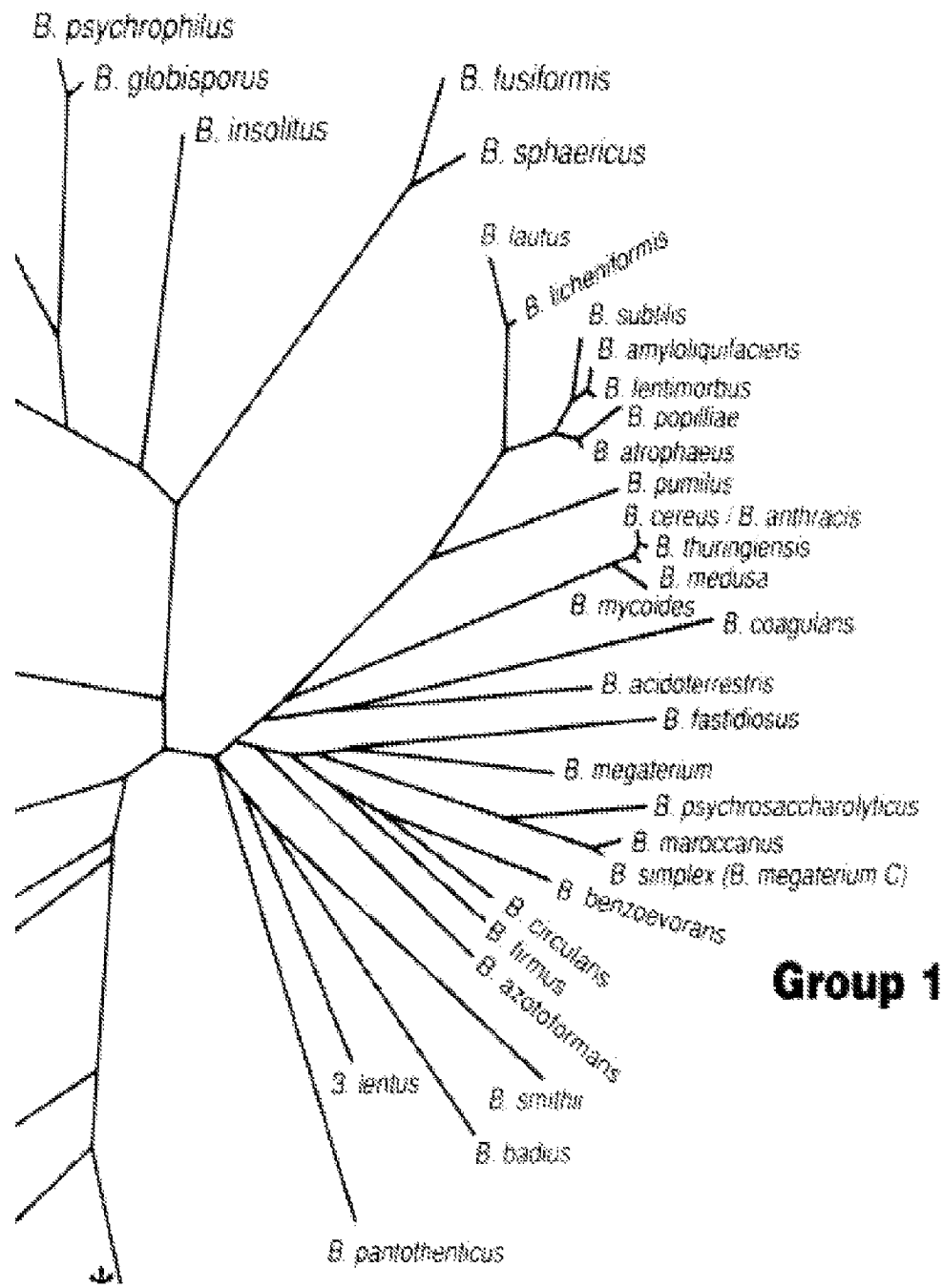

USE OF AN ANTHRANILIC DIAMIDE DERIVATIVES WITH HETEROAROMATIC AND HETEROCYCLIC SUBSTITUENTS IN COMBINATION WITH A BIOLOGICALCONTROL AGENT

CROSS REFERENCE TO RELATED APPLICATIONS

This application is a §371 National Stage Application of PCT/EP2012/075840, filed Dec. 17, 2012, which claims priority to EP 11194336.1, filed Dec. 19, 2011.

BACKGROUND

Field of the Invention

The present invention relates to the use of anthranilic diamide derivatives with heteroaromatic and heterocyclic substituents in combination with a biological control agent as well as to a preparation method of compositions containing anthranilic diamide derivatives and a selected biological control agent, and compositions containing anthranilic diamide derivatives and at least one biological control agent.

Description of Related Art

It is already known that certain anthranilamides (e.g. WO 01/70671, WO 03/015519, WO 03/016284, WO 03/015518, WO 03/024222, WO 03/016282, WO 03/016283, WO 03/062226, WO 03/027099, WO 04/027042, WO 04/033468, WO 2004/046129, WO 2004/067528, WO 2005/118552, WO 2005/077934, WO 2005/085234, WO 2006/023783, WO 2006/000336, WO 2006/040113, WO 2006/111341, WO 2007/006670, WO 2007/024833, WO 2007/020877) are useful for combating harmful pests which occur in agriculture. Several methods to apply such compounds are described therein.

However, environmental and economic requirements imposed in modern-day crop protection agents are continually increasing. This is particularly true with regard to the spectrum of action, toxicity, selectivity, application rate, and formation of residues. Additionally, when applying agrochemicals, there are always the problems with resistances. Thus, there is a constant need for developing new, alternative plant protection agents which in some areas at least help to fulfil the abovementioned requirements. Moreover, there is a constant need to develop novel plant treatment agents which are particularly environmentally friendly. Also, as concerns regarding a possible impact of agrochemicals on the environment and the health of humans and animals are growing in the public opinion, efforts have to be made to reduce the amount of agrochemicals applied.

SUMMARY

The inventors now surprisingly found that specific anthranilic diamide derivatives can be combined with selected biological control agents and thus satisfying above mentioned needs. The inventors even found that a synergistic activity increase occurs by combining selected anthranilic diamide derivatives with selected biological control agents.

Thus, the invention is directed to the use of anthranilic acid diamide derivatives with heteroaromatic and heterocyclic substituents of formula (I)

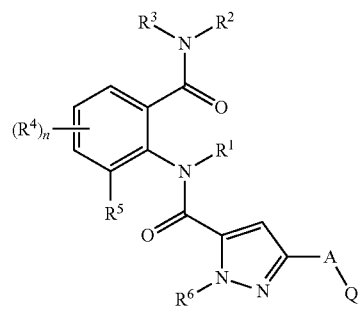

in which $R^1$ represents hydrogen, amino or hydroxyl or represents $C_1$-$C_6$-alkyl, $C_2$-$C_6$-alkenyl, $C_2$-$C_6$-alkynyl or $C_3$-$C_6$-cycloalkyl each of which is unsubstituted or substituted one or more times by identical or different substituents selectable independently of one another from halogen, cyano, nitro, hydroxyl, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$alkoxycarbonyl or $C_2$-$C_6$-alkylcarbonyl, $R^3$ represents hydrogen or represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkyl sulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from amino, $C_3$-$C_6$-cycloalkylamino or a 5- or 6-membered heteroaromatic ring, $R^3$ likewise further represents $C_3$-$C_{12}$-cycloalkyl, $C_3$-$C_{12}$-cycloalkyl-$C_1$-$C_6$-alkyl and $C_4$-$C_{12}$-bicycloalkyl, the substituents being selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, $R^2$ and $R^3$ can be joined to one another via two to six carbon atoms and form a ring which where appropriate additionally contains a further nitrogen, sulphur or oxygen atom and where appropriate may be substituted one to four times by $C_1$-$C_2$-alkyl, halogen, cyano, amino or $C_1$-$C_2$-alkoxy, $R^2$ and $R^3$ further together represent =S($C_1$-$C_4$-alkyl)$_2$ or =S(O)($C_1$-$C_4$-alkyl)$_2$, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$s, via adjacent carbon atoms, form a ring which represents —(CH$_2$)$_3$—, —(CH$_2$)$_4$—, —(CH$_2$)$_5$—, —(CH=CH—)$_2$—, —OCH$_2$O—, —O(CH$_2$)$_2$O—, —OCF$_2$O—, —(CF$_2$)$_2$O—, —O(CF$_2$)$_2$O—, —(CH=CH—CH=N)— or —(CH=CH—N=CH)—, two $R^4$s further, via adjacent carbon atoms, form the following fused rings, which where appropriate are substituted one or more times by identical or different substituents selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino, n represents 0 to 3, $R^5$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

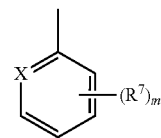

$R^6$ further represents $C_3$-$C_6$-cycloalkoxy, $R^7$ represents independently at each occurrence hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 4, X represents N, CH, CF, CCl, CBr or CI, A represents —CH$_2$—, —CH$_2$O—, —CH$_2$OCH$_2$—, —CH$_2$S—, —CH$_2$SCH$_2$—, —CH$_2$N($C_1$-$C_6$-alkyl)-, —CH$_2$N($C_1$-$C_6$-alkyl)CH$_2$—, —CH[CO$_2$($C_1$-$C_6$-alkyl)]-, —CH(CN)—, —CH($C_1$-$C_6$-alkyl)-, —C(di-$C_1$-$C_6$-alkyl)-, —CH$_2$CH$_2$— or —C=NO($C_1$-$C_6$-alkyl)-, Q represents a 5- or 6-membered heteroatomatic ring or an aromatic 8-, 9- or 10-membered fused heterobicyclic ring system, the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, CO$_2$H, CO$_2$NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, Q further represents a 5- or 6-membered heteroaromatic or heterocyclic ring or an aromatic 8-, 9- or 10-membered fused heterobicyclic ring system, the ring or the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, CO$_2$H, CO$_2$NH$_2$, NO$_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, NO$_2$, OH, $C_1$-$C_4$-alkoxy, $C_1$-$C_4$-haloalkoxy substituents, whereas the compounds of the general formula (I) also encompass N-oxides and salts, in combination with at least one biological control agent selected from bacteria, in particular spore-forming bacteria, fungi or yeasts, protozoas todes, and botanical extracts, or products produced by microorganisms including proteins or secondary metabolites, optionally in the presence of inoculants, for reducing overall damage of plants and plant parts as well as losses in harvested fruits or vegetables caused by insects, nematodes and phytopathogens.

BRIEF DESCRIPTION OF THE FIGURE

FIG. 1, shows the genealogy of bacteria that can be used in the present invention.

DETAILED DESCRIPTION OF A PREFERRED EMBODIMENT

Preferred radical definitions for the formula (I) given above are specified below.

$R^1$ preferably represents hydrogen, $C_1$-$C_6$-alkyl, $C_2$-$C_6$-alkenyl, $C_2$-$C_6$-alkynyl, $C_3$-$C_6$-cycloalkyl, cyano($C_1$-$C_6$-alkyl), $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkylthio-$C_1$-$C_4$-alkyl, $C_1$-$C_4$-alkylsulphinyl-$C_1$-$C_4$-alkyl or $C_1$-$C_4$-alkylsulphonyl-$C_1$-$C_4$-alkyl.

$R^1$ more preferably represents hydrogen, methyl, cyclopropyl, cyanomethyl, methoxymethyl, methylthiomethyl, methylsulphinylmethyl or methylsulphonylmethyl.

$R^1$ very preferably represents hydrogen.

$R^2$ preferably represents hydrogen or $C_1$-$C_6$-alkyl.

$R^2$ more preferably represents hydrogen or methyl.

$R^2$ very preferably represents hydrogen.

$R^3$ preferably represents hydrogen or represents $C_1$-$C_6$-alkyl, $C_1$-$C_6$-alkoxy, $C_2$-$C_6$-alkenyl or $C_2$-$C_6$-alkynyl each of which is unsubstituted or substituted one or more times by identical or different substituents selectable from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further preferably represents $C_3$-$C_{12}$-cycloalkyl and $C_4$-$C_{10}$-bicycloalkyl, the substituents being selectable independently of one another from halogen, cyano, nitro, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ more preferably represents hydrogen or represents $C_1$-$C_6$-alkyl, $C_1$-$C_6$-alkoxy each of which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further more preferably represents $C_3$-$C_6$-cycloalkyl which is unsubstituted or substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_{1-4}$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ very preferably represents $C_1$-$C_4$-alkyl (methyl, ethyl, n-propyl, isopropyl, n-butyl, isobutyl, sec-butyl or tert-butyl) or cyano-$C_1$-$C_3$-alkyl (cyanomethyl, 1-cyanoethyl, 2-cyanoethyl, 1-cyano-n-propyl, 2-cyano-n-propyl, 3-cyano-n-propyl, 1-cyanoisopropyl, 2-cyanoisopropyl).

$R^3$ with particular preference represents methyl, isopropyl or cyanomethyl.

$R^4$ preferably represents hydrogen, $C_1$-$C_4$-alkyl, $C_1$-$C_4$-haloalkyl, halogen, cyano, $C_1$-$C_4$-alkoxy, $C_1$-$C_4$-haloalkoxy, $C_1$-$C_4$-alkylthio or $C_1$-$C_4$-haloalkylthio.

Preferably, moreover, two adjacent radicals $R^4$ represent —$(CH_2)_3$—, —$(CH_2)_4$—, —$(CH_2)_5$—, —$(CH=CH—)_2$—, —$OCH_2O$—, —$O(CH_2)_2O$—, —$OCF_2O$—, —$(CF_2)_2O$—, —$O(CF_2)_2O$—, —$(CH=CH—CH=N)$— or —$(CH=CH—N=CH)$—.

$R^4$ more preferably represents hydrogen, $C_1$-$C_4$-alkyl, $C_1$-$C_2$-haloalkyl, halogen, cyano or $C_1$-$C_2$-haloalkoxy.

More preferably, moreover, two adjacent radicals $R^4$ represent —$(CH_2)_4$—, —$(CH=CH—)_2$—, —$O(CH_2)_2O$—, —$O(CF_2)_2O$—, —$(CH=CH—CH=N)$— or —$(CH=CH—N=CH)$—.

$R^4$ very preferably represents hydrogen, methyl, trifluoromethyl, cyano, fluorine, chlorine, bromine, iodine or trifluoromethoxy. Very preferably, moreover, two adjacent radicals $R^4$ represent —$(CH_2)_4$—, or —$(CH=CH—)_2$—.

$R^4$ with particular preference represents chlorine or bromine, $R^4$ further with particular preference represents iodine or cyano. With particular preference, moreover, two adjacent radicals $R^4$ represent —$(CH=CH—)_2$—.

$R^5$ preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl.

$R^5$ more preferably represents $C_1$-$C_4$-alkyl, $C_3$-$C_6$-cycloalkyl, $C_1$-$C_4$-haloalkyl, $C_1$-$C_6$-halocycloalkyl, $C_2$-$C_6$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, fluorine, chlorine, bromine, iodine, cyano, nitro or $C_3$-$C_6$-trialkylsilyl.

$R^5$ very preferably represents methyl, fluorine, chlorine, bromine or iodine.

$R^5$ with particular preference represents methyl or chlorine.

$R^6$ preferably represents $C_1$-$C_6$-alkyl or

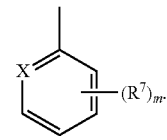

$R^6$ further preferably represents $C_3$-$C_6$-cycloalkoxy.
$R^6$ more preferably represents methyl or

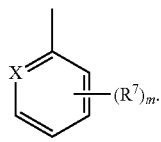

$R^7$ independently at each occurrence preferably represents hydrogen, halogen, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-haloalkylsulphonyl or ($C_1$-$C_4$-alkyl)$C_1$-$C_4$-alkoxyimino, $R^7$ independently at each occurrence more preferably represents hydrogen, halogen or $C_1$-$C_4$-haloalkyl, $R^7$ very preferably represents fluorine, chlorine or bromine, $R^7$ with particular preference represents chlorine.

m preferably represents 1, 2 or 3, m more preferably represents 1 or 2, m very preferably represents 1, X preferably represents N, CH, CF, CCl, CBr or CI, X more preferably represents N, CH, CF, CCl or CBr, X very preferably represents N, CCl or CH.

A preferably represents —$CH_2$—, —$CH_2O$—, —$CH_2OCH_2$—, —$CH_2S$—, —$CH_2SCH_2$—, —$CH_2N$($C_1$-$C_6$-alkyl)-, —$CH_2N(C_1$-$C_6$-alkyl)$CH_2$—, —CH(CN)—, —C(di-$C_1$-$C_6$-alkyl)-, —$CH_2CH_2$— or —C=NO($C_1$-$C_6$-alkyl)-, A more preferably represents —$CH_2$—, —CH($CH_3$), C($CH_3$)$_2$ or $CH_2CH_2$, A further more preferably represents —CH(CN)—, A very preferably represents $CH_2$ or CH($CH_3$), A with particular preference represents $CH_2$.

Q preferably represents an optionally mono- or polysubstituted 5- or 6-membered aromatic heterocyclic ring of series Q-1 to Q-53 or an aromatic 9-membered fused heterobicyclic ring system Q-54 to Q-56, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy.

Q further preferably represents an optionally mono- or polysubstituted 5- or 6-membered aromatic heterocyclic ring of series Q-1 to Q-53 and Q-58 to Q-59, an aromatic 9-membered fused heterobicyclic ring system Q-54 to Q-56 and also represents a 5-membered heterocyclic ring Q-60 to Q-61, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be substituted where appropriate one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy or $C_1$-$C_4$-haloalkoxy substituents, Q more preferably represents an optionally mono- or polysubstituted 5- or 6-membered aromatic heterocyclic ring of series Q-36 to Q-40 or an aromatic 9-membered fused heterobicyclic ring system Q-54 to Q-56, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy.

Q further more preferably represents an optionally mono- or polysubstituted 5- or 6-membered aromatic heterocyclic ring of series Q-36 to Q-40 and Q-58 to Q-59, an aromatic 9-membered fused heterobicyclic ring system Q-54 to Q-56 and also represents a 5-membered heterocyclic ring Q-60 to Q-61, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from $C_1$-$C_3$-alkyl, $C_1$-$C_3$-haloalkyl, $C_1$-$C_2$-alkoxy, halogen, cyano, hydroxyl, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q further very preferably represents an optionally mono- or polysubstituted aromatic heterocyclic ring of series Q-37, Q-38, Q-39, Q-40, Q-58 and Q-59, and also represents a 5-membered heterocyclic ring Q-60, the substituents being selectable independently of one another from $C_1$-$C_3$-alkyl, $C_1$-$C_3$-haloalkyl, halogen, cyano, nitro or $C_1$-$C_2$-haloalkoxy, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy or $C_1$-$C_4$-haloalkoxy substituents, Q with particular preference represents an aromatic heterocyclic ring Q-37, Q-40, Q-58 and Q-59 which is unsubstituted or substituted once, twice or three times on carbon atoms, and also represents a 5-membered heterocyclic ring Q-60, the substituents being selectable independently of one another from chlorine, fluorine, iodine, bromine, cyano, trifluoromethyl and pentafluoroethyl, or the substituents being selectable independently of one another from phenyl, it being possible for the phenyl ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$ or $C_1$-$C_4$-haloalkoxy substituents, Q further with particular preference represents an optionally mono- or polysubstituted aromatic heterocyclic ring of series Q-37, Q-40, Q-58 and Q-59, and also represents a 5-membered heterocyclic ring Q-60, the substituents being selectable independently of one another from chlorine, fluorine, iodine, cyano, trifluoromethyl and pentafluoroethyl, or the substituents being selectable independently of one another from phenyl, it being possible for the phenyl ring to be unsubstituted or substituted one or more times by identical or different chlorine, fluorine, iodine, bromine, cyano, trifluoromethyl and pentafluoroethyl substituents,

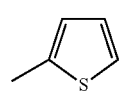
Q-1

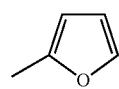
Q-2

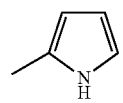
Q-3

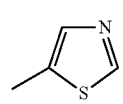
Q-4

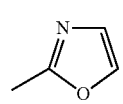
Q-5

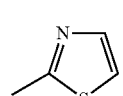
Q-6

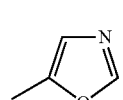
Q-7

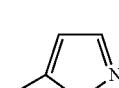
Q-8

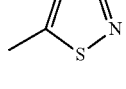
Q-9

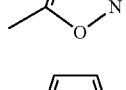
Q-10

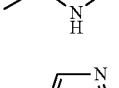
Q-11

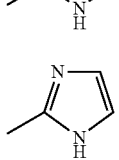
Q-12

-continued

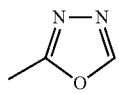
Q-13

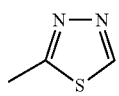
Q-14

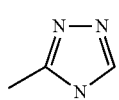
Q-15

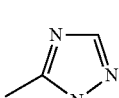
Q-16

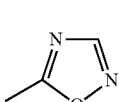
Q-17

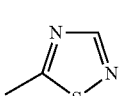
Q-18

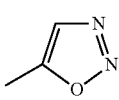
Q-19

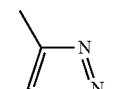
Q-20

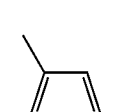
Q-21

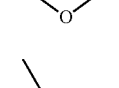
Q-22

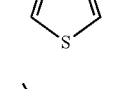
Q-23

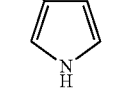
Q-24

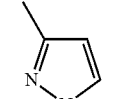
Q-25

-continued
| | |
|---|---|
| Q-26 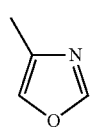 | Q-38 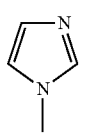 |
| Q-27 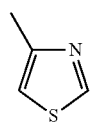 | Q-39 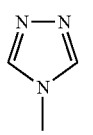 |
| Q-28 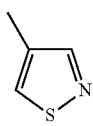 | Q-40 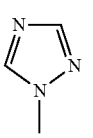 |
| Q-29 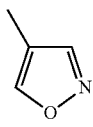 | Q-41 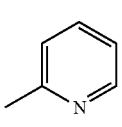 |
| Q-30 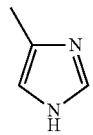 | Q-42 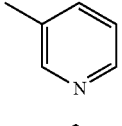 |
| Q-31 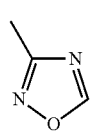 | Q-43 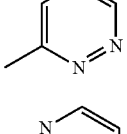 |
| Q-32 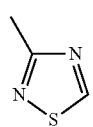 | Q-44 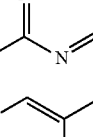 |
| Q-33 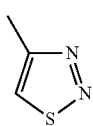 | Q-45 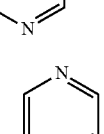 |
| Q-34 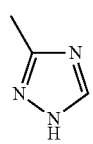 | Q-46 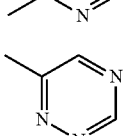 |
| Q-35 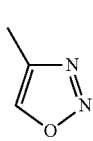 | Q-47 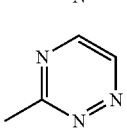 |
| Q-36 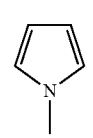 | Q-48 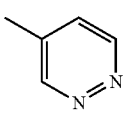 |
| Q-37 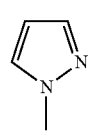 | Q-49 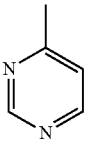 |

Q-51 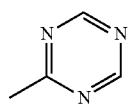

Q-52 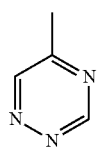

Q-53 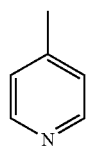

Q-54 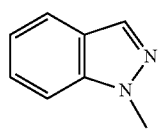

Q-55 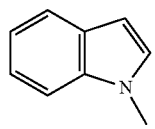

Q-56 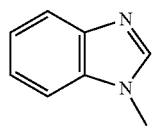

Q-57 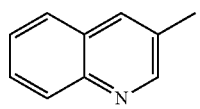

Q-58 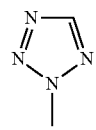

Q-59 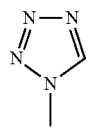

Q-60 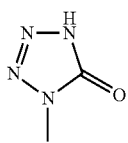

Q-61 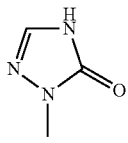

Q-62 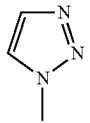

Q-63 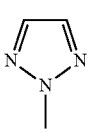

Emphasis is given to the use of compounds of the formula (I-1) according to the invention

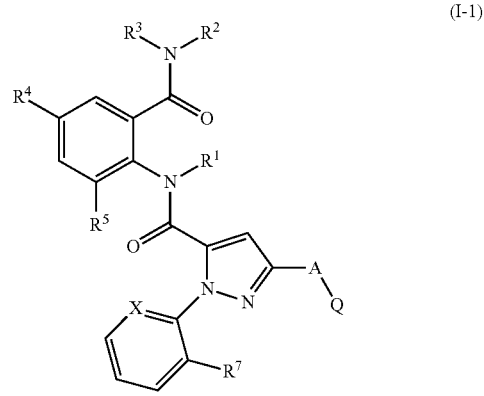

(I-1)

in which $R^1$, $R^2$, $R^3$, $R^4$, $R^5$, $R^7$, A, Q and X have the above-indicated general, preferred, more preferred, very preferred and particularly preferred definitions.

The compounds of the formula (I) or (I-1) may be present in the form of different regioisomers: for example in the form of mixture of compounds with the definition of Q62 and Q63 or in the form of mixtures of Q58 and Q59. The invention therefore also encompasses compounds of the formula (I) or (I-1) where $Q_Y$ is defined as Q62 and Q63, and Q58 and Q59, in different mixing ratios; to be used in combination with at least one biological control agent selected from bacteria, in particular spore-forming bacteria, fungi or yeasts, protozoas, viruses, entomopathogenic nematodes and botanical extracts, or products produced by microorganisms including proteins or secondary metabolites, optionally in the presence of inoculants, for reducing overall damage of plants and plant parts as well as losses in harvested fruits or vegetables caused by insects, nematodes and phytopathogens.

Preference is given to mixing ratios of compounds of the formula (I) in which the $Q_Y$ radical is Q62 or Q58 to compounds of the formula (I) in which the Qy radical is Q63 or Q59 of 60:40 to 99:1, more preferably of 70:30 to 97:3, even more preferably of 80:20 to 99:1. Especially preferred are the following mixing ratios of a compound of the formula (I) where $Q_Y$ is defined as Q62 or Q58 to the compound of the formula (I) where $Q_Y$ is defined as Q63 or Q59: 80:20; 81:19; 82:18; 83:17; 84:16; 85:15; 86:14; 87:13; 88:12; 89:11; 90:10, 91:9; 92:8; 93:7; 94:6, 95:5, 96:4, 97:3, 98:2, 99:1.

More preferred is the use of the compounds (I-1-1) to (I-1-60) according to the invention
(I-1-1)
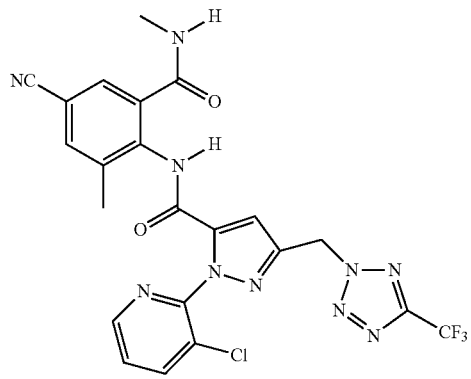
(I-1-2)
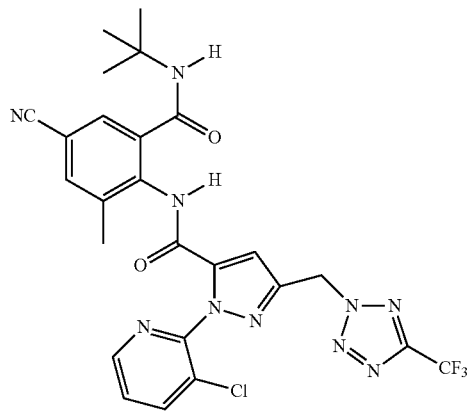
(I-1-3)
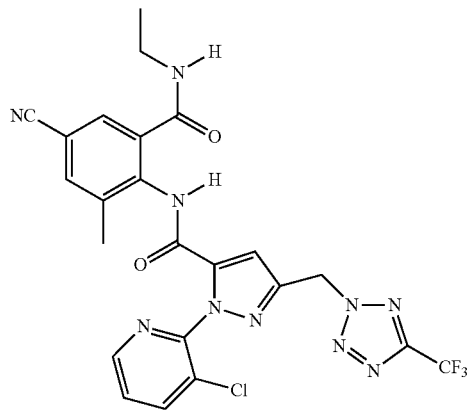
(I-1-4)
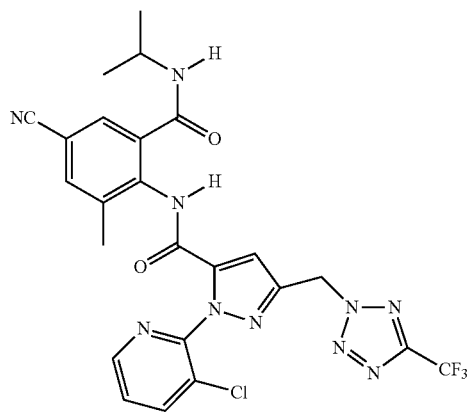
(I-1-5)
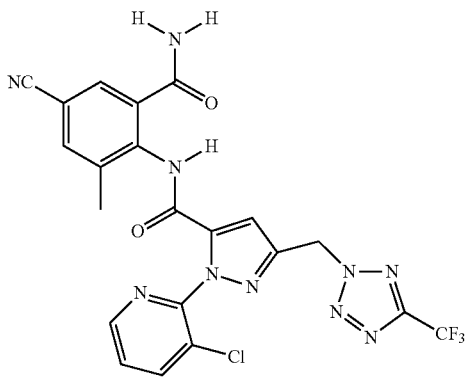
(I-1-6)
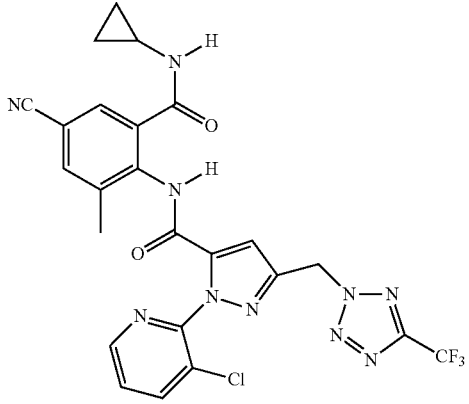
(I-1-7)
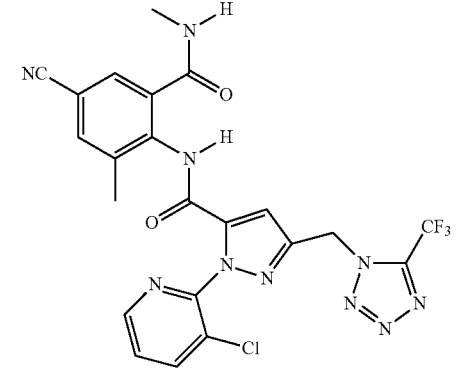
(I-1-8)
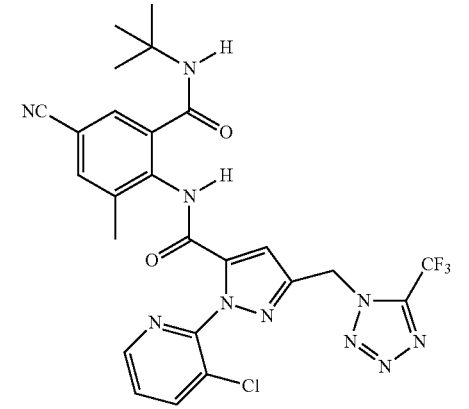

-continued
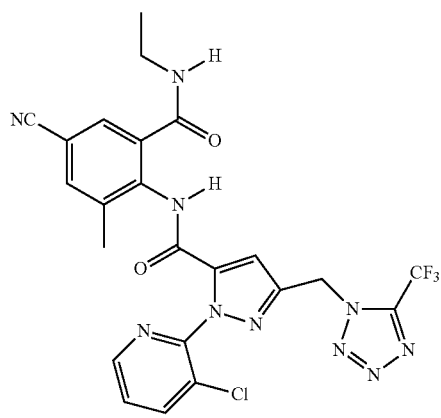
(I-1-9)
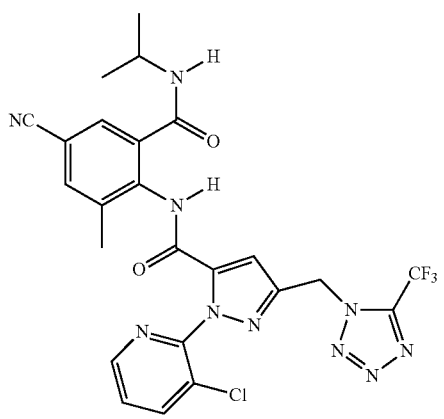
(I-1-10)
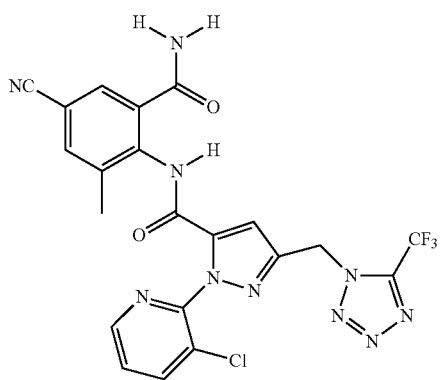
(I-1-11)
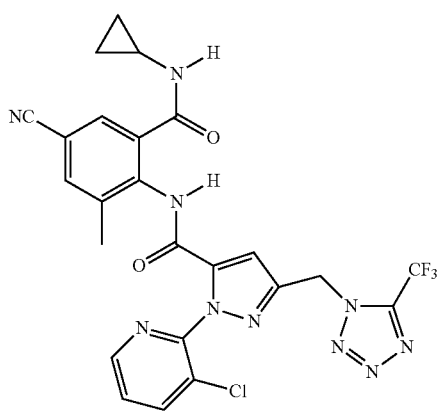
(I-1-12)
-continued
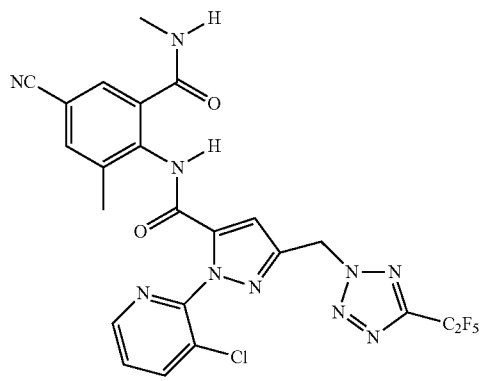
(I-1-13)
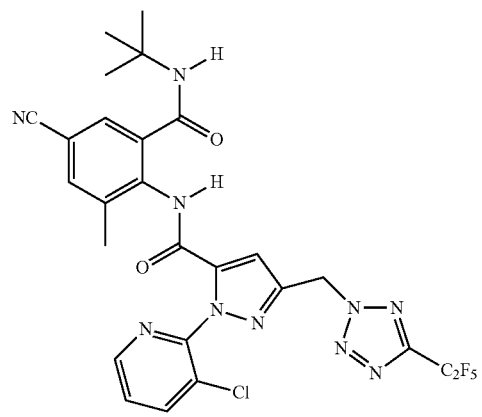
(I-1-14)
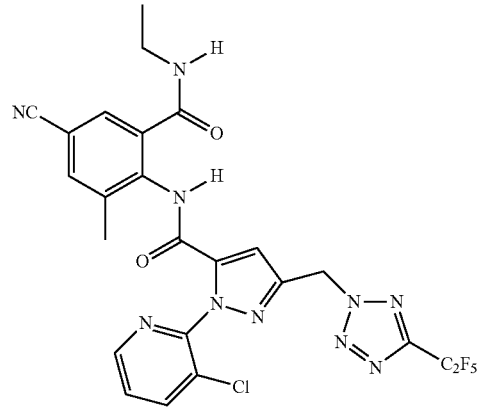
(I-1-15)
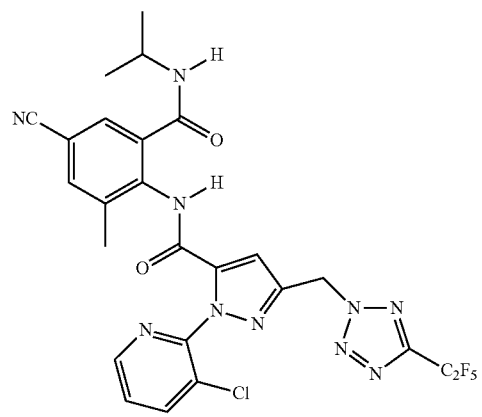
(I-1-16)

-continued
(I-1-17)
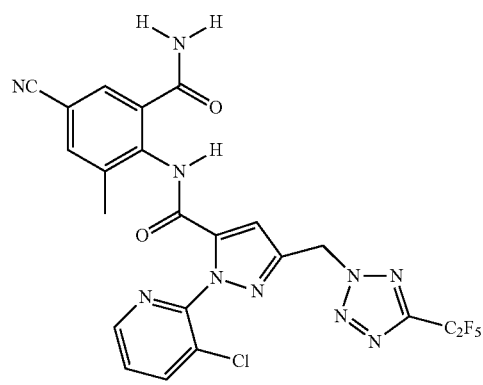
(I-1-18)
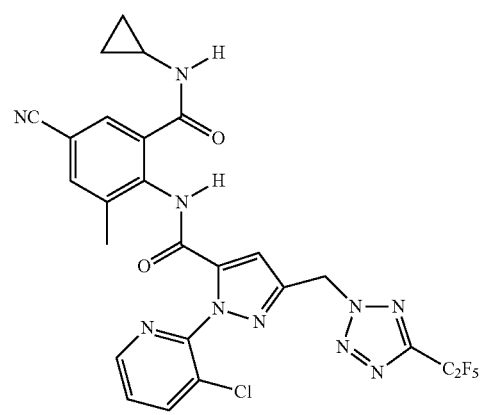
(I-1-19)
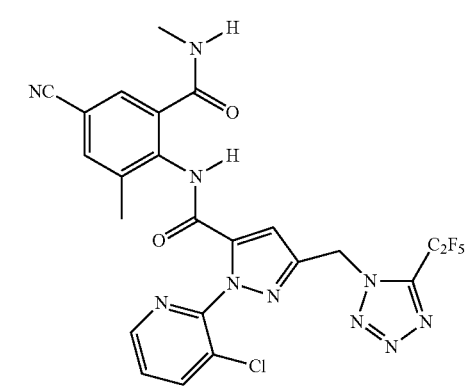
(I-1-20)
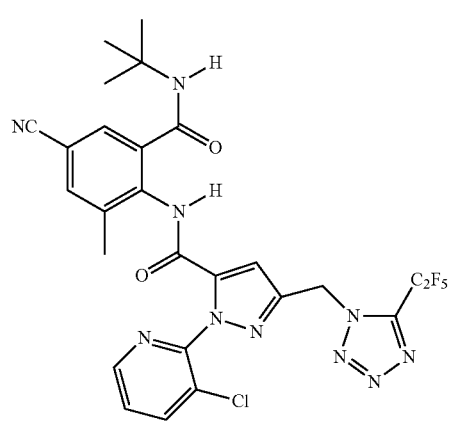
-continued
(I-1-21)
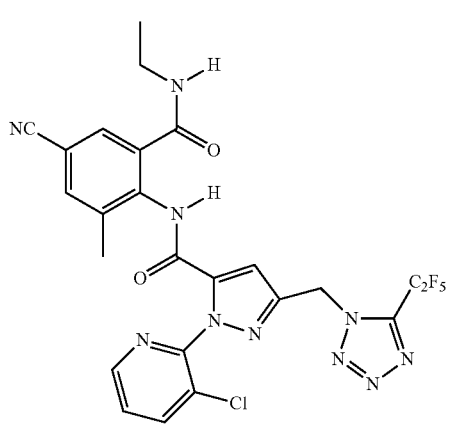
(I-1-22)
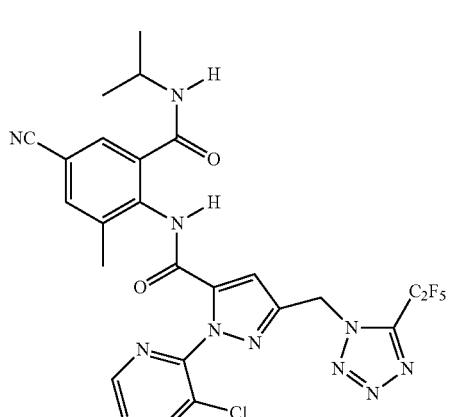
(I-1-23)
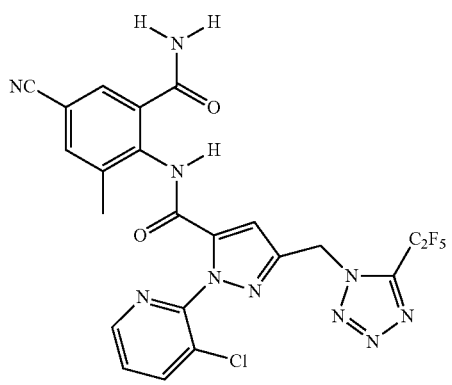
(I-1-24)
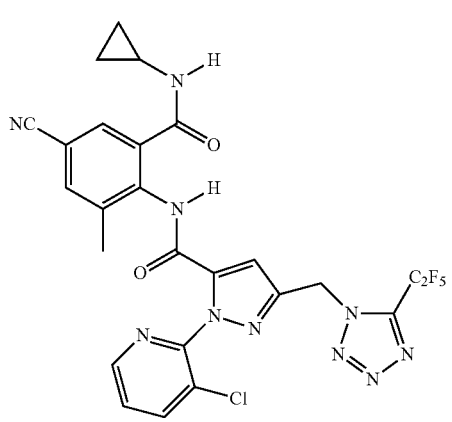

(I-1-25)
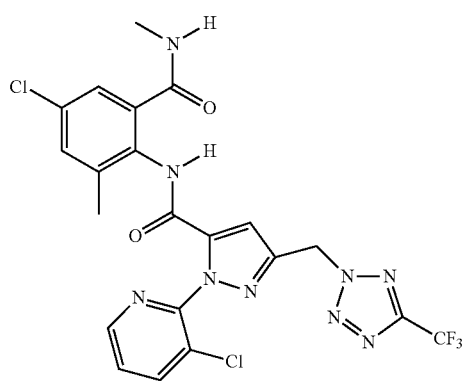
(I-1-26)
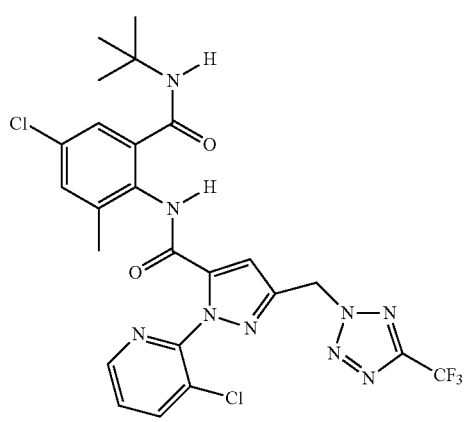
(I-1-27)
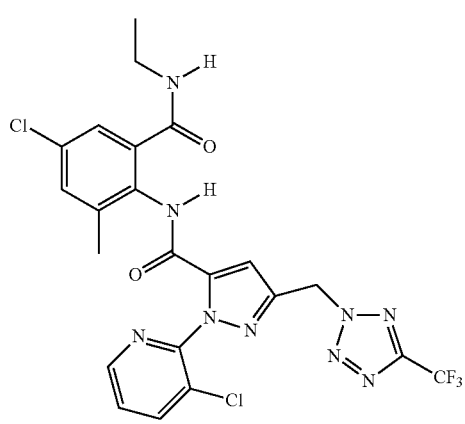
(I-1-28)
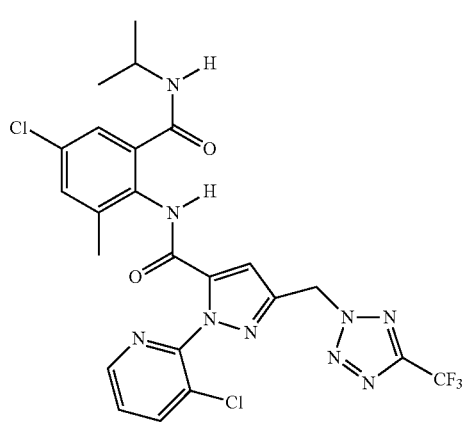
(I-1-29)
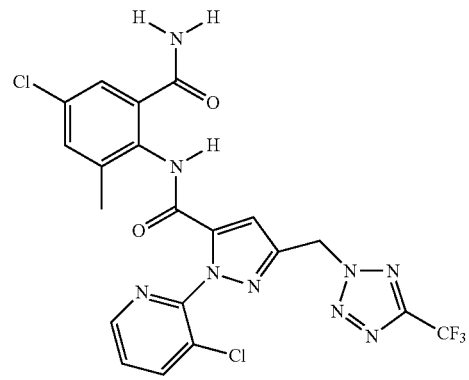
(I-1-30)
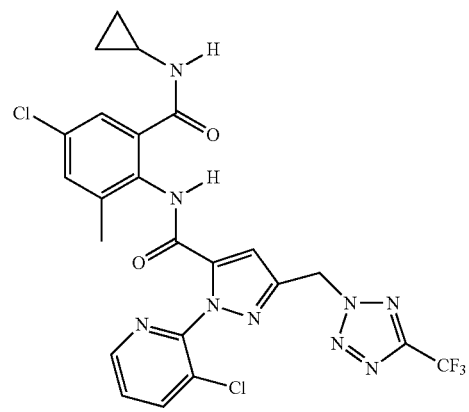
(I-1-31)
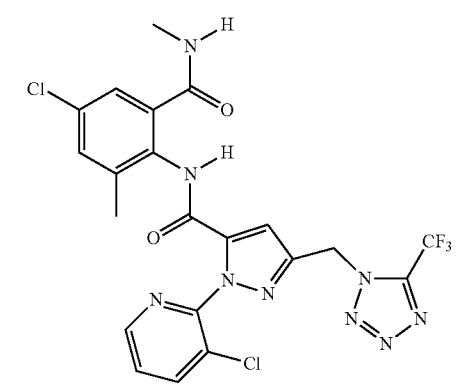
(I-1-32)
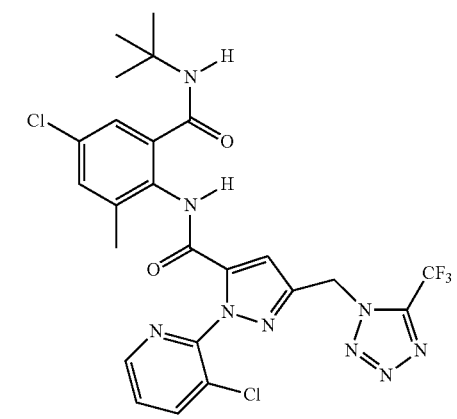

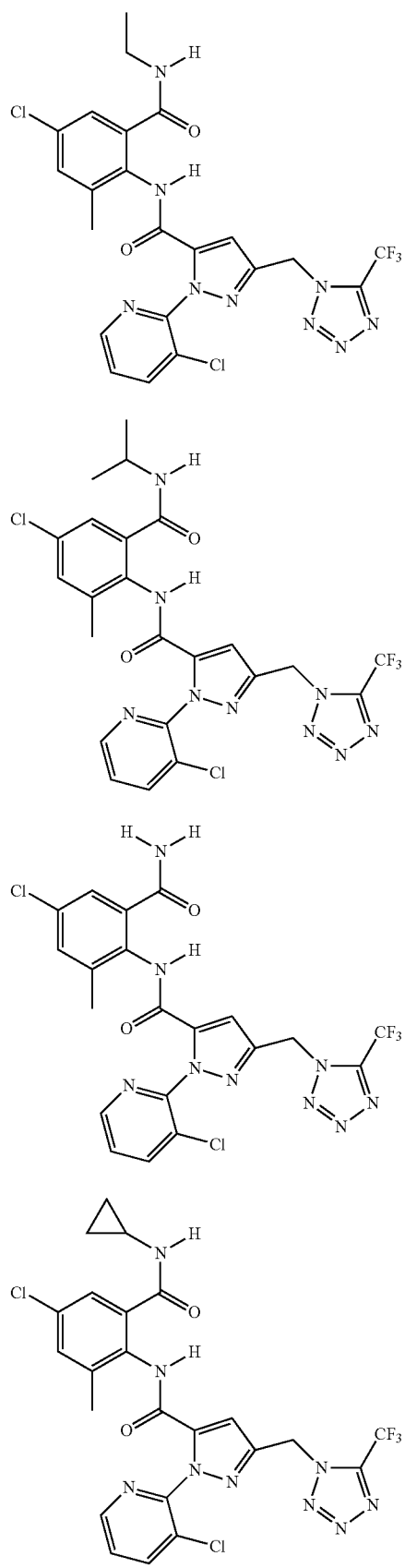
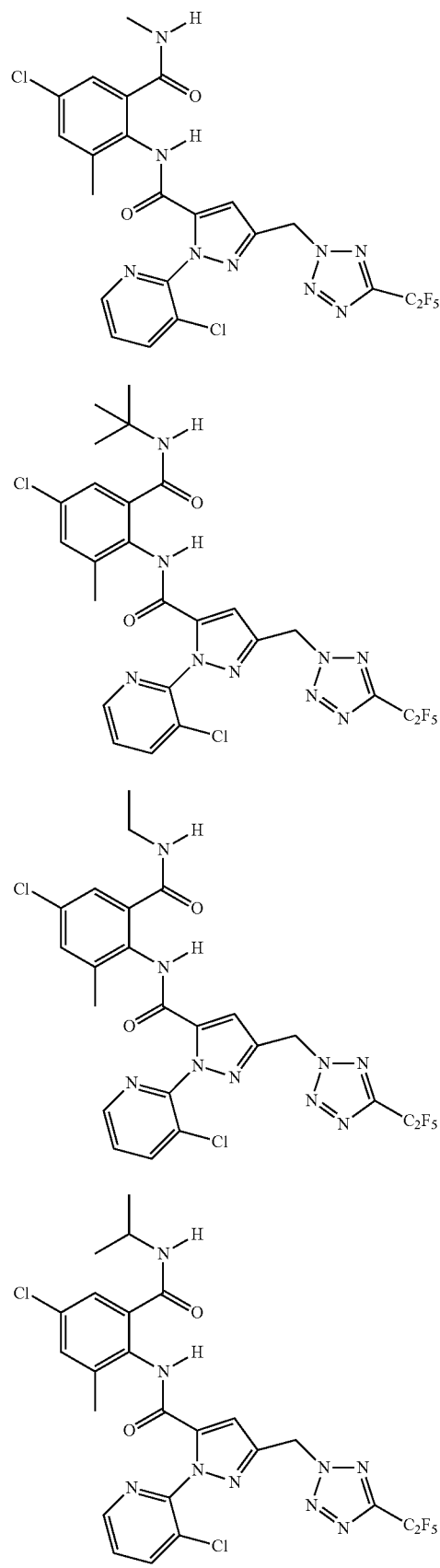

-continued
(I-1-41)
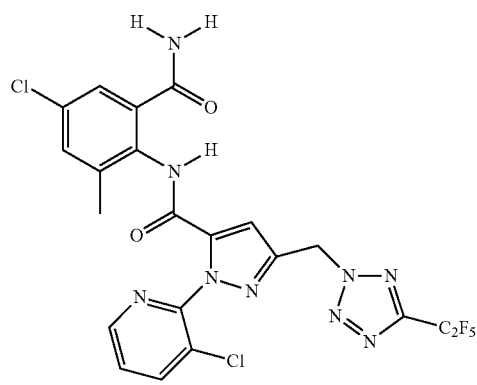
(I-1-42)
(I-1-43)
(I-1-44)
-continued
(I-1-45)
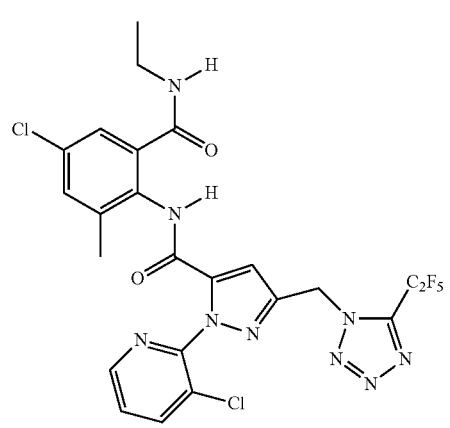
(I-1-46)
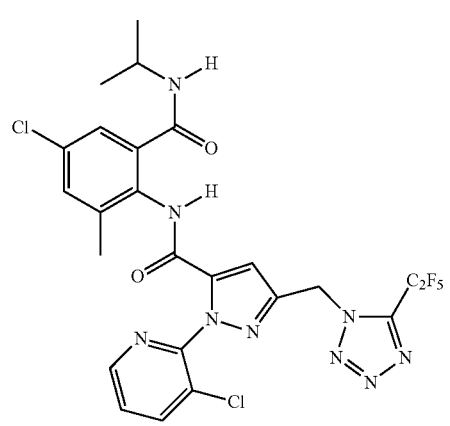
(I-1-47)
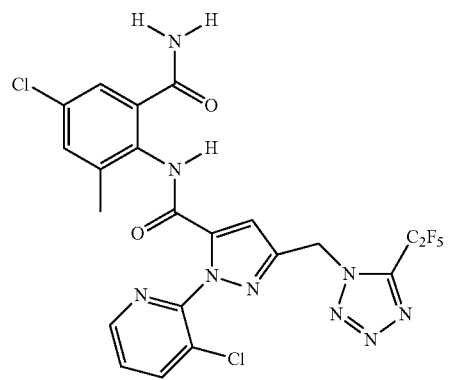
(I-1-48)
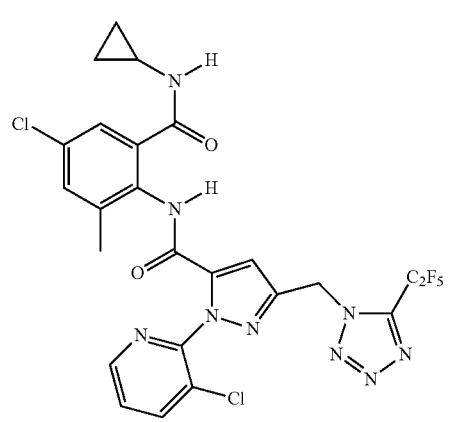

(I-1-49)
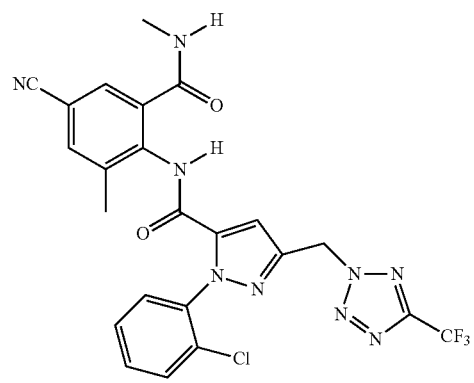
(I-1-50)
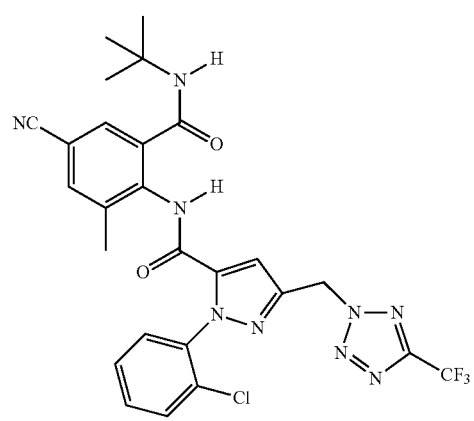
(I-1-51)
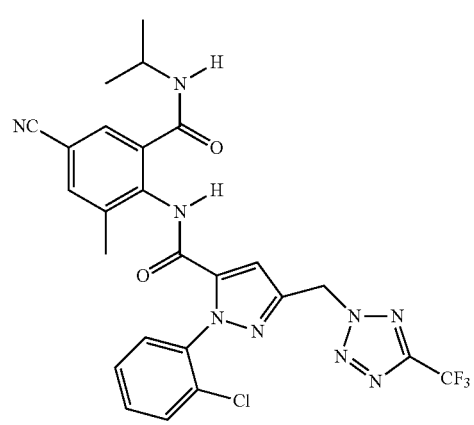
(I-1-52)
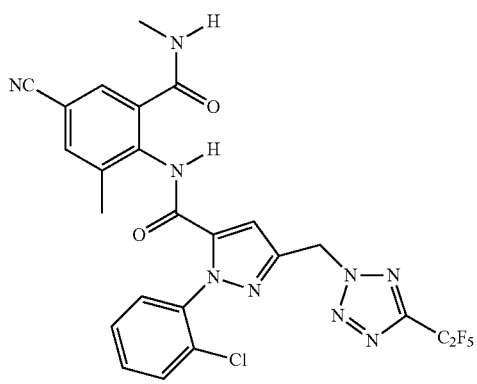
(I-1-53)
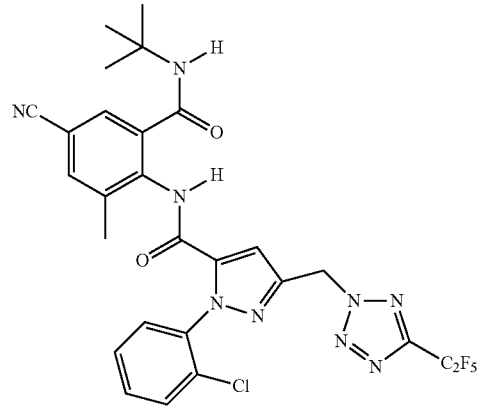
(I-1-54)
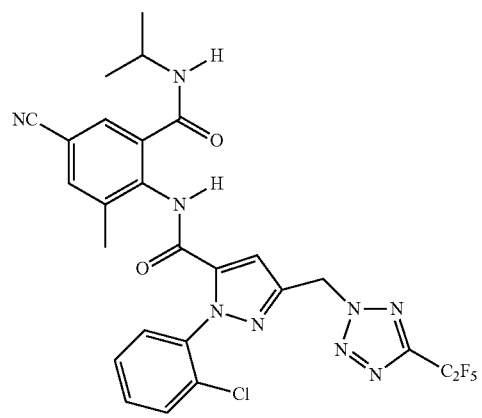
(I-1-55)
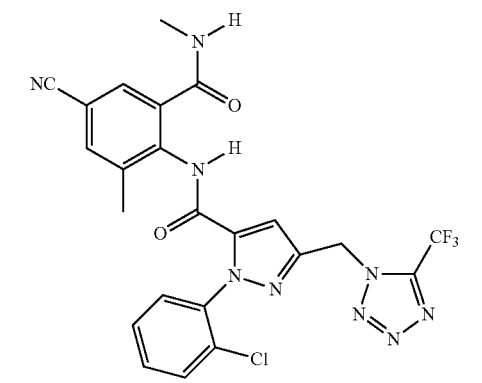
(I-1-56)
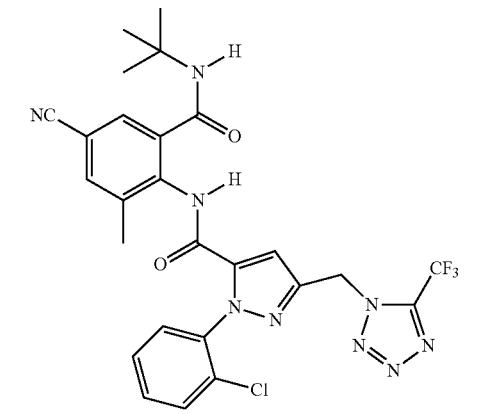

(I-1-57)
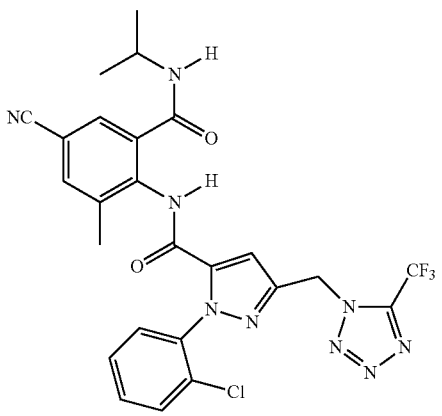

(I-1-58)
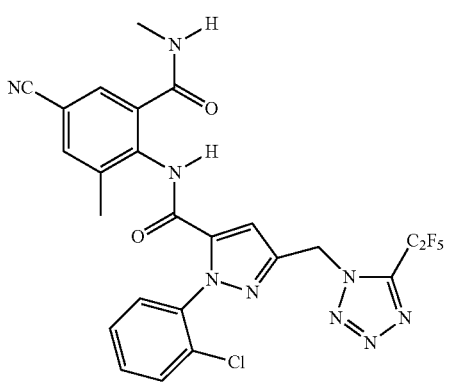

(I-1-59)
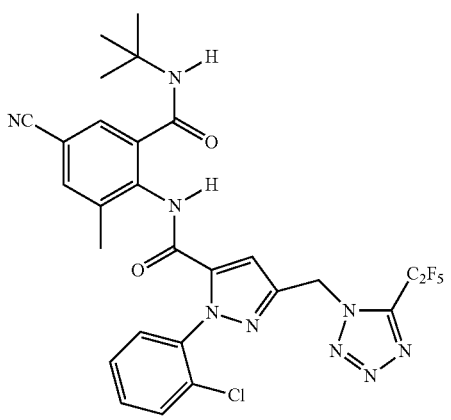

(I-1-60)
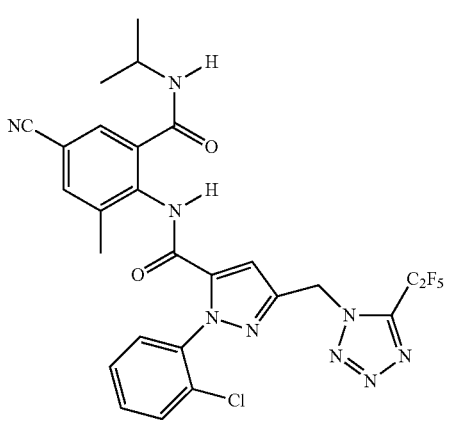

Additionally more preferred is the use of the following mixtures of compounds of the formula (I-1-1) to (I-1-60) according to the invention
(I-1-1)/(I-1-7), (I-1-2)/(I-1-8), 1-1-3/1-1-9, I-1-4/1-1-10, I-1-5/1-1-11, I-1-6/1-1-12, I-1-13/I-1-1-19, 1-1-14/1-1-20, I-1-15/I-1-21, I-1-16/I-1-22, I-1-17/I-1-23, I-1-18/I-1-24, 1-1-25/1-1-31, 1-1-26/1-1-32, I-1-27/I-1-33, 1-1-28/1-1-34, I-1-29/I-1-35, I-1-30/I-1-36, 1-1-37/1-1-43, 1-1-38/1-1-44, I-1-39/I-1-45, I-1-40/I-1-46, I-1-41/I-1-47, I-1-42/I-1-48, I-1-49/I-1-55, I-1-50/I-1-56, I-1-51/I-1-57, I- 1-52/I-1-58, I-1-53/I-1-59, I-1-54/I-1-60.

The compound of formula (I-1-1), (I-1-2), as well as the mixtures (I-1-1)/(I-1-7), (I-1-2)/(I-1-8) are particularly preferred to be used or employed according to the invention, thus, also if not mentioned explicitly, the naming of compounds of formula (I) or compounds (I-1) always implies that the compound of formula (I-1-1), (I-1-2), as well as the mixtures (I-1-1)/(I-1-7), (I-1-2)/(I-1-8) are preferred.

According to the invention, the biological control agent may be employed or used in any physiologic state such as active or dormant. Dormant yeast e.g. may be supplied for example frozen, dried, or lyophilized.

The invention is further directed to the preparation of a composition containing compounds of formula (I) and at least one biological control agent selected from bacteria, in particular spore-forming bacteria, fungi or yeasts, protozoas, viruses, entomopathogenic nematodes, and botanical extracts or products produced by microorganisms, and optionally an inoculant, for reducing overall damage of plants and plant parts as well as losses in harvested fruits or vegetables caused by insects, nematodes and phytopathogens.

The invention is also directed to a method for reducing overall damage of plants and plant parts as well as losses in harvested fruits or vegetables caused by insects, nematodes and phytopathogens comprising the step of simultaneously or sequentially applying compounds of formula (I) and at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally at least an inoculant, on the plant, plant parts, harvested fruits or vegetables.

The invention is also directed to the use of compounds of formula (I) and at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally at least an inoculant, for the treatment of seeds or a plant emerging from the seed.

Moreover the invention is directed to a method for protecting seeds comprising the step of simultaneously or sequentially applying compounds of formula (I) and at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally at least an inoculant, on a seed or a plant emerging from the seed. The method is further called "seed treatment".

The compounds of formula (I) and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally an inoculant may be applied in any desired manner, such as in the form of a seed coating, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow.

Reducing the overall damage of plants and plant parts often results in healthier plants and/or in an increase in plant vigor and yield.

The use or the method to use compounds of formula (I) and at least one biological control agent selected from bacteria, in particular spore-forming bacteria, fungi or yeasts, protozoas, viruses, entomopathogenic nematodes and botanical extracts or products produced by microorganisms including proteins or secondary metabolites, and optionally an inoculant simultaneously or sequentially includes the following application methods, namely both before mentioned components may be formulated into a single, stable composition with an agriculturally acceptable shelf life (so called "solo-formulation"), or being combined before or at the time of use (so called "combined-formulations").

If not mentioned otherwise, the expression "combination" stands for the various combinations of compounds of formula (I) and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, in a solo-formulation, in a single "ready-mix" form, in a combined spray mixture composed from solo-formulations, such as a "tank-mix", and especially in a combined use of the single active ingredients when applied in a sequential manner, i.e. one after the other within a reasonably short period, such as a few hours or days, e.g. 2 hours to 7 days. The order of applying compound of formula (I) and the biological control agent selected from bacteria, in particular spore-forming bacteria, fungi or yeasts, protozoas, viruses, entomopathogenic nematodes and botanical extracts or products produced by microorganisms including proteins or secondary metabolites, and optionally the inoculant, is not essential for working the present invention. Accordingly, the term "combination" also encompasses the presence of compounds of formula (I) and the biological control agent selected from bacteria, in particular spore-forming bacteria, fungi or yeasts, protozoas, viruses, entomopathogenic nematodes and botanical extracts or products produced by microorganisms including proteins or secondary metabolites, and optionally the inoculant, on or in a plant to be treated or its surrounding, habitat or storage space, e.g. after simultaneously or consecutively applying compounds of formula (I) and the biological control agent selected from bacteria, in particular spore-forming bacteria, fungi or yeasts, protozoas, viruses, entomopathogenic nematodes and botanical extracts or products produced by microorganisms including proteins or secondary metabolites, and optionally the inoculant to a plant its surrounding, habitat or storage space.

If the compounds of formula (I) and the biological control agent selected from bacteria, in particular spore-forming bacteria, fungi or yeasts, protozoas, viruses, entomopathogenic nematodes and botanical extracts, or products produced by microorganisms including proteins or secondary metabolites, and optionally an inoculant, are employed or used in a sequential manner, it is preferred to treat the plants or plant parts (which includes seeds and plants emerging from the seed), harvested fruits and vegetables according to the following method: Firstly applying the compound of formula (I) on the plant or plant parts, and secondly applying the biological control agent selected from bacteria, in particular spore-forming bacteria, fungi or yeasts, protozoas, viruses, entomopathogenic nematodes and botanical extracts, or products produced by microorganisms including proteins or secondary metabolites, and optionally the inoculant, to the same plant or plant parts. The time periods between the first and the second application within a (crop) growing cycle may vary and depend on the effect to be achieved. For example, the first application is done to prevent an infestation of the plant or plant parts with insects, nematodes and/or phytopathogens (this is particularly the case when treating seeds) or to combat the infestation with insects, nematodes and/or phytopathogens (this is particularly the case when treating plants and plant parts) and the second application is done to prevent or control the infestation with insects, nematodes and/or phytopathogens. Control in this context means that the biological control agent is not able to fully exterminate the pests or phytopathogenic fungi but is able to keep the infestation on an acceptable level.

By following the before mentioned steps, a very low level of residues of the compound of formula (I) on the treated plant, plant parts, and the harvested fruits and vegetables can be achieved.

If not mentioned otherwise the treatment of plants or plant parts (which includes seeds and plants emerging from the seed), harvested fruits and vegetables with the compound of formula (I), preferably compound (I-1-1), (I-1-2), as well as the mixtures (I-1-1)/(I-1-7), (I-1-2)/(I-1-8), and the biological control agent selected from bacteria, in particular spore-forming bacteria, fungi or yeasts, protozoas, viruses, entomopathogenic nematodes, and botanical extracts, or products produced by microorganisms including proteins or secondary metabolites, and optionally the inoculant, is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the compound of formula (I), preferably compound (I-1-1), (I-1-2), as well as the mixtures (I-1-1)/(I-1-7), (I-1-2)/(I-1-8), and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, as solo-formulation or combined-formulations by the ultra-low volume method, or to inject the compound of formula (I), preferably compound (I-1-1), (I-1-2), as well as the mixtures (I-1-1)/(I-1-7), (I-1-2)/(I-1-8), and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, as a composition or as sole-formulations into the soil (in-furrow).

In general, the terms "spore-forming bacteria", "fungi" or "yeasts" comprise all stages of bacteria, fungi and yeast including resting spores, conidia, blastospores, filamentous stages and other inactive forms of said organisms which can yield in active organisms. Thus, in one embodiment, said organisms are comprised in form of spores in a formulation, e.g., a solo- or combined-formulation.

In general, the term "nematode" comprises eggs, larvae, juvenile and mature forms of said organism. Thus, in one embodiment, said organisms are comprised in form of eggs, larvae, juvenile or mature form in a formulation, e.g., a solo- or combined-formulation.

A solo- or combined-formulation is the formulation which is applied to the plants to be treated (e.g., in a greenhouse, on a field, in a wood), e.g., a tank formulation comprising the biological control agent in accordance with the present invention and a compound of formula (I) or a liquid or solid formulation comprising said biological control agent which is applied prior, after or in parallel with a compound of formula (I) to a plant to be treated.

The term "plant to be treated" encompasses every part of a plant including its root system and the material—e.g., soil or nutrition medium—which is in a radius of at least 10 cm, 20 cm, 30 cm around the bole of a plant to be treated or which is at least 10 cm, 20 cm, 30 cm around the root system of said plant to be treated, respectively.

In the case of seed treatment, the treatment can be carried out by applying the compound of formula (I), preferably compound (I-1-1), (I-1-2), as well as the mixtures (I-1-1)/(I-1-7), (I-1-2)/(I-1-8), and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, as a solution, a powder (for dry seed treatment), a water-soluble powder (for slurry seed treatment), or by incrusting, by coating with one or more layers containing the compound of formula (I), preferably compound (I-1-1), (I-1-2), as well as the mixtures (I-1-1)/(I-1-7), (I-1-2)/(I-1-8), and the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant.

As already mentioned before, using a compound of formula (I) and at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally an inoculant, as a combination is advantageous. The broadening of the activity spectrum to other agricultural pests (i.e. insects, acari, nematodes, and phytopathogens) and, for example to resistant strains of such agricultural pests and/or plant diseases can be achieved.

Also according to the invention, the compound of formula (I) and the biological control agent selected from bacteria, in particular spore-forming bacteria, fungi or yeasts, protozoas, viruses, entomopathogenic nematodes and botanical extracts, or products produced by microorganisms including proteins or secondary metabolites, and optionally an inoculant, can be used in a lower application rate and still achieve the sufficient control of the agricultural pests and/or plant diseases. This is particularly visible if application rates for the before mentioned compounds or biological control agents are used where the individual compounds or biological control agents show no or virtually no activity. The invention can also result in an advantageous behaviour during formulation or during use, for example during grinding, sieving, emulsifying, dissolving or dispensing; improved storage stability and light stability, advantageous residue formation, improved toxicological or ecotoxicological behaviour, improved properties of the plant, for example better growth, increased harvest yields, a better developed root system, a larger leaf area, greener leaves, stronger shoots, less seed required, lower phytotoxicity, mobilization of the defense system of the plant, good compatibility with plants. Moreover, even an enhanced systemic action of the compound of formula (I) or the biological control agent selected from bacteria, in particular spore-forming bacteria, fungi or yeasts, protozoas, viruses, entomopathogenic nematodes and botanical extracts or products produced by microorganisms including proteins or secondary metabolites, is higher and/or a persistency of the fungicidal, insecticidal, acaricidal and/or nematicidal action is expected.

Using compounds of formula (I) and at least one biological control agent selected from bacteria, in particular spore-forming bacteria, fungi or yeasts, protozoas, viruses, entomopathogenic nematodes and botanical extracts or products produced by microorganisms including proteins or secondary metabolites, and optionally an inoculant, as a combination is particularly suitable for treating seed. A large part of the damage to crop plants caused by harmful agricultural pests and/or plant diseases is triggered by an infection of the seed during storage or after sowing as well as during and after germination of the plant. This phase is particularly critical since the roots and shoots of the growing plant are particularly sensitive, and even small damage may result in a weak plant (unhealthy plant), reduced yield and even in the death of the plant.

The control of pests and/or phytopathogens by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of agrochemicals employed in such a way as to provide maximum protection for the seed and the germinating plant from attack by agricultural pests, but without damaging the plant itself by the active compound employed. In particular, methods for the treatment of seed should also take into consideration the intrinsic insecticidal properties of plants in order to achieve optimum protection of the seed and the germinating plant with a minimum of agrochemicals being employed.

As already mentioned, the compounds of formula (I) and the biological control agent selected from bacteria, in particular spore-forming bacteria, fungi or yeasts, protozoas, viruses, entomopathogenic nematodes and botanical extracts or products produced by microorganisms including proteins or secondary metabolites, and optionally an inoculant can be employed or used according to the invention as a solo- or a combined-formulation. Such formulations may include agriculturally suitable auxiliaries, solvents, carriers, surfactants and/or extenders.

According to the invention biological control agents which are summarized under the term "bacteria" include spore-forming, root-colonizing bacteria, or bacteria useful as bioinsecticide, biofungicide and/or nematicide. Examples of such bacteria to be used or employed according to the invention are:

(1.1) *Bacillus agri*, (1.2) *Bacillus aizawai*, (1.3) *Bacillus albolactis*, (1.4) *Bacillus amyloliquefaciens*, in particular the strain IN937a, or strain FZB42 (DSM 23117) (product known as RhizoVital®) or strain B3 or var *amyloliquefaciens* D747, (1.5) *Bacillus cereus*, in particular spores of *Bacillus cereus* strain CNCM I-1562 (cf. U.S. Pat. No. 6,406,690), (1.6) *Bacillus coagulans*, (1.7) *Bacillus endoparasiticus*, (1.8) *Bacillus endorhythmos*, (1.9) *Bacillus azotoformans*, (1.10) *Bacillus kurstaki*, (1.11) *Bacillus lacticola*, (1.12) *Bacillus lactimorbus*, (1.13) *Bacillus lactis*, (1.14) *Bacillus laterosporus*, (1.15) *Bacillus lentimorbus*, (1.16) *Bacillus licheniformis*, (1.17) *Bacillus medusa*, (1.18) *Bacillus megaterium*, (1.19) *Bacillus metiens*, (1.20) *Bacillus natto*, (1.21) *Bacillus nigrificans*, (1.22) *Bacillus popillae*, (1.23) *Bacillus pumilus*, in particular strain GB34 (ATCC 700814) (products known as Yield Shield®, or strain QST 2808 (NRRL B-30087) (products known as Sonata QST 2808®) or strain BU F-33 (product known as Integral F-33), (1.24) *Bacillus siamensis*, (1.26) *Bacillus subtilis*, in particular strain GB03 (products known as Kodiak®) or strain QST 713 (NRRL B-21661) (products known as Serenade QST 713®, Serenade® Max, Serenade® Soil, Serenade® ASO, Rhapsody), or *Bacillus subtilis* var. *amyloliquefaciens* strain FZB24 (products known as Taegro®, Rhizopro, FZB24) or strain MBI 600 (products known as Subtilex), (1.27) *Bacillus thuringiensis*, in particular *Bacillus thuringiensis* subsp. *morrisoni* or *Bacillus thuringiensis* var san diego or *Bacillus thuringiensis* subsp. *thuringiensis* (serotype 1) MPPL002, or *Bacillus thuringiensis* var. *aegyptii*, or *Bacillus thuringiensis* var. *colmeri*, or *Bacillus thuringiensis* var. *darmstadiensis*, or *Bacillus thuringiensis* var. *Dendrolimus*, or *Bacillus thuringiensis* var. *Galleriae*, or *Bacillus thuringiensis* var. *Japonensis*, or *Bacillus thuringiensis* strain HD-1 (products known as Dipel® ES), or *Bacillus thuringiensis* var 7216, or *Bacillus thuringiensis* var T36, (1.28) *Bacillus uniflagellatus*, (1.29) *Delftia acidovorans*, in particular strain RAY209 (products known as BioBoost®), (1.30) *Lysobacter antibioticus*, in particular strain 13-1 (cf. Biological Control 2008, 45, 288-296), (1.31) *Pasteuria penetrans* (formerly *Bacillus penetrans*), (1.32) *Pseudomonas chlororaphis*, in particular strain MA 342 (products known as Cedomon), (1.33) *Pseudomonas proradix* (products known as Proradix®), (1.34) *Streptomyces galbus*, in particular strain K61 (products known as Mycostop®, cf. Crop Protection 2006, 25, 468-475), (1.35) *Streptomyces griseoviridis* (products known as Mycostop®), (1.36) *Bacillus lautus*, (1.37) *Bacillus atrophaeus*, (1.38) *Bacillus anthracia*, (1.39) *Bacillus mycoides*, in particular isolate J/BmJ or strain 683, (1.40) *Bacillus acidoterrestris*, (1.41) *Bacillus fastidiosus*, (1.42) *Bacillus psychrosaccharolyticus*, (1.43) *Bacillus maroccanus*, (1.44) *Bacillus megaterium* C, (1.45) *Bacillus pantothenticus*, (1.46) *Bacillus lentus*, (1.47) *Bacillus badius*, (1.48) *Bacillus smithi*, (1.49) *Bacillus circulars*, (1.51) *Paenibacillus polymyxa*, (1.52) *Paenibacillus popilliae* (formerly *Bacillus popilliae*), (1.53) *Serratia entomophila*, (1.54) *Chromobacterium subtsugae* in particular strain PRAA4-1T (product known as Grandevo), (1.55) *Acinetobacter* sp., (1.56) *Pasteuria usgae* (product known as Econem™ Biological Nematicide), (1.57) *Bacillus chitinosporus* (product known as Ne-Plex), (1.58) *Pseudomonas cepacia* (ex *Burkholderia cepacia*) in particular strains M54 and strain J82, and (1.59) *Bacillus nematocida*, (1.60) *Xenorhabdus luminescence*, (1.61) *Brevibacillus laterosporus* (also known as *Bacillus laterosporus*), in particular strain 64 or strain G4 or strain 1111 or strain 1645 or strain 1647, (1.62) *Corynebacterium paurometabolum*, (1.63) *Lactobacillus acidophilus* (products known as Fruitsan®), (1.64) *Paenibacillus alvei*, in particular strain T36 or strain III3DT-1A or strain III2E or strain 46C3 or strain 2771, (1.65) *Paenibacillus macerans*, (1.66) *Pasteuria nishizawae*, in particular strain Pn1 (product known as *Pasteuria nishizawae*-liquid formulation), (1.67) *Pasteuria ramosa*, (1.68) *Pasteuria thomei*, (1.69) *Pseudomonas aeruginosa*, (1.70) *Pseudomonas aureofaciens*, (1.71) *Pseudomonas fluorescens* (products known as BlightBan or Victus), (1.72) *Pseudomonas putida*, (1.73) *Pseudomonas resinovorans* (products known as Solanacure), ((1.74) *Pseudomonas syringae* (products known as Bio-Save), (1.75) *Serratia marcescens*, in particular strain SRM (MTCC8708) or strain R35, (1.76) *Streptomyces candidus* (products known as BioAid), (1.77) *Streptomyces lydicus*, in particular strain WYCD108 and strain WYEC108 (products known as ActinovateSP), (1.78) *Streptomyces saraceticus*, (1.79) *Streptomyces venezuelae*, (1.80) *Xenorhabdus nematophila*, (1.81) *Agrobacterium radiobacter*, (1.82) *Bacillus mojavensis*, especially strain CECT-7666, *Pantoea agglomerans*, in particular strain E325 (products known as Bloomtime Biological FD Biopesticide), (1.83) *Streptomyces colombiensis*, (1.84) *Streptomyces* sp. WYE 20 (KCTC 0341BP) and WYE 324 (KCTC 0342BP), (1.85) *Bacillus brevis* (also known as *Brevibacillus brevis*), (1.86) *Erwinia carotovora* (also known as *Pectobacterium carotovorum*) *carotovora* (product known as Biokeeper), (1.87) *Xanthomonas campestris* pv vesicatoria (product known as Camprico), (1.88) *Pasteuria reniformis*, in particular strain Pr3 (product known as *Pasteuria reniformis*—liquid formulation), (1.89) *Burkholderia spec* strain A396 (product known as MBI-206 EP or MBI-206-TGAI)

*Bacillus* (abbreviation: B.) is a genus of rod-shaped, gram-positive bacteria, which can produce endospores under stressful environmental conditions. The single species of this genus differ strongly with respect to their usability in the area of plant protection

*Bacillus subtilis*, for example the strains GB03 and QST 713, as well as *Bacillus amyloliquefaciens*, strain FZB 42, are species with phytopathogenic properties. These bacteria are applied to the soil and/or to the leaves.

From the given bacteria (1.1) to (1.89) or (1.1) to (1.60), such bacteria or mutants thereof that have an insecticidal or plant growth promoting activity are preferred to be used or employed in the present invention, in one embodiment in combination with compound (I-1-1), (I-1-2), as well as the mixtures (I-1-1)/(I-1-7), (I-1-2)/(I-1-8), optionally in the presence of an inoculant.

From the given bacteria (1.1) to (1.89) or (1.1) to (1.60), such bacteria or mutants thereof that have an insecticidal, fungicidal and/or nematicidal activity are preferred to be used or employed in the present invention, in one embodiment in combination with compound (I-1-1), (I-1-2), as well as the mixtures (I-1-1)/(I-1-7), (I-1-2)/(I-1-8), optionally in the presence of an inoculant.

In one embodiment, from the given bacteria (1.1) to (1.89) or (1.1) to (1.60), the bacteria given under the numbers (1.4), (1.5), (1.6), (1.15), (1.16), (1.17), (1.18), (1.22), (1.23), (1.26), (1.27) and (1.36) to (1.44) are to be used or employed in the present invention, such as in combination with compound (I-1-1), (I-1-2), as well as the mixtures (I-1-1)/(I-1-7), (I-1-2)/(I-1-8), optionally in the presence of an inoculant. These bacteria belong to the class of group 1 bacteria as disclosed in Ash et al., 1991, Lett Appl Microbiology 13, 202-206. The genealogy of group 1 bacteria is also shown in FIG. 1. Notably, Group 1 bacteria can be divided into subgroups depending on the ramification within the group. Thus, subgroup (1) consists of *B. pantothenticus, B. lentus, B. badius,* and *B. smithi*; subgroup (2) consists of *B. azotoformans, B. circulars, B. benzoevorans, B. simplex, B. marrocanus, B. psychrosaccharolyticus, B. megaterium* and *B. fastidiosus*; and subgroup (3) consists of *B. lautus, B. licheniformis, B. subtilis, B. amyloliquifaciens, B. lentimorbus, B. popilliae, B. atrophaeus, B. pumilus, B. cereus, B. anthracis, B. medusa, B. mycoides, B. coagulans,* and *B. acidoterrestris*. Subgroup (3) can be further divided into subgroup (3a) consisting of *B. lautus, B. licheniformis, B. subtilis, B. amyloliquifaciens, B. lentimorbus, B. popilliae,* and *B. atrophaeus*; subgroup (3b) consisting of *B. pumilus, B. cereus, B. anthracis, B. medusa,* and *B. mycoides*; and subgroup (3c) consisting of *B. coagulans,* and *B. acidoterrestris*.

In one embodiment, the bacteria of subgroup (3), (3a), (3b) or (3c) are to be used or employed in the present invention, such as in combination with compound (I-1-1), (I-1-2), as well as the mixtures (I-1-1)/(I-1-7), (I-1-2)/(I-1-8), optionally in the presence of an inoculant.

In another embodiment, the bacteria of subgroup (1) are to be used or employed in the present invention, such as in combination with compound (I-1-1), (I-1-2), as well as the mixtures (I-1-1)/(I-1-7), (I-1-2)/(I-1-8), optionally in the presence of an inoculant.

In another embodiment, the bacteria given under the numbers (1.4), (1.5), (1.23), and (1.26) are to be used or employed in the present invention, such as in combination with compound (I-1-1), (I-1-2), as well as the mixtures (I-1-1)/(I-1-7), (I-1-2)/(I-1-8), optionally in the presence of an inoculant.

From the given bacteria (1.4), the bacteria (1.4a) *Bacillus amyloliquefaciens* strain IN937a, and (1.4b) *Bacillus amyloliquefaciens* strain FZB42 are used or employed in the present invention, in one embodiment in combination with compound (I-1-1), (I-1-2), as well as the mixtures (I-1-1)/(I-1-7), (I-1-2)/(I-1-8), optionally in the presence of an inoculant.

From the given bacteria (1.5), the bacterium (1.5a) *Bacillus cereus* strain CNCM I-1562 especially spores are used or employed in the present invention, in one embodiment in combination with compound (I-1-1), (I-1-2), as well as the mixtures (I-1-1)/(I-1-7), (I-1-2)/(I-1-8), optionally in the presence of an inoculant.

From the given bacteria (1.23), the bacterium (1.23a) *Bacillus pumilus* strain GB34 or (1.23b) *Bacillus pumilus* strain QST 2808 or (1.23c) *Bacillus pumilus* strain BU F-33 is used or employed in the present invention, in one embodiment in combination with compound (I-1-1), (I-1-2), as well as the mixtures (I-1-1)/(I-1-7), (I-1-2)/(I-1-8), optionally in the presence of an inoculant.

From the given bacteria (1.26), the bacteria (1.26a) *Bacillus subtilis* strain GB03, (1.26b) *Bacillus subtilis* strain QST 713 and (1.26c) *Bacillus subtilis* var. *amyloliquefaciens* strain FZB24 are used or employed in the present invention in one embodiment in combination with compound (I-1-1), (I-1-2), as well as the mixtures (I-1-1)/(I-1-7), (I-1-2)/(I-1-8), optionally in the presence of an inoculant.

According to the invention biological control agents that are summarized under the term "fungi" or "yeasts" are:

(2.1) *Ampelomyces quisqualis*, in particular strain AQ 10 (product known as AQ 10®), (2.2) *Aureobasidium pullulans*, in particular blastospores of strain DSM14940 or blastospores of strain DSM 14941 or mixtures thereof (product known as Blossom Protect®), (2.3) *Beauveria bassiana*, in particular strain ATCC 74040 (products known as Naturalis®) or strain ATP02 (DSM 24665) or strain GHA (products known as BOTANIGARD® 22WP, MYCOTROL® O) or strain CG716 (product known as BoveMax), (2.4) *Candida oleophila*, in particular strain O (products known as Nexy®) or strain I-182 (products known as ASPIRE®, Decco I-182), (2.6) *Coniothyrium minitans*, in particular strain CON/M/91-8 (DSM-9660) (products known as Contans®), (2.7) *Dilophosphora alopecuri* (products known as Twist Fungus®), (2.8) *Gliocladium catenulatum*, in particular strain J1446 (products known as Prestop®), (2.9) *Lecanicillium lecanii* (formerly known as *Verticillium lecanii*), in particular conidia of strain KV01 (products known as Mycotal®, Vertalec®) or strain DAOM198499 or strain DAOM216596, (2.10) *Metarhizium anisopliae*, in particular strain F52 (DSM 3884, ATCC 90448) (products known as BIO 1020. MET52) or var. acridum isolate IMI 330189/ARSEF 7486 (products known as Green Muscle®), (2.11) *Metschnikovia fructicola*, in particular the strain NRRL Y-30752 (products known as Shemer®), (2.12) *Microsphaeropsis ochracea* (products known as Microx®), (2.13) *Muscodor albus*, in particular strain QST 20799 (products known as QRD300), (2.14) *Nomuraea rileyi*, in particular strains SA86101, GU87401, SR86151, CG128 and VA9101, (2.15a) *Paecilomyces lilacinus*, in particular spores of *P. lilacinus* strain 251 (AGAL 89/030550) (products known as BioAct®, cf. Crop Protection 2008, 27, 352-361), or (2.15b) *Paecilomyces fumosoroseus* (also known as *Isaria fumosorosea*), in particular strain apopka 97 (products known as PreFeRal® WG), (2.16) *Penicillium bilaii*, in particular strain ATCC22348 (products known as JumpStart®, PB-50, Provide), (2.17) *Pichia anomala*, in particular strain WRL-076, (2.18) *Pseudozyma flocculosa*, in particular strain PF-A22 UL (products known as Sporodex® L), (2.19) *Pythium oligandrum*, in particular strain DV74 (products known as Polyversum), (2.20) *Trichoderma asperellum*, in particular strain ICC 012 (products known as Bioten®) or strain SKT-1 (products known as ECO-HOPE®) or strain T34/CECT No. 20417 (products known as T34 Biocontrol) or strain SF04, (2.21) *Trichoderma harzianum*, in particular *T. harzianum* T39 (products known as Trichodex®) or strain T-22 (products known as PLANTSHIELD®T-22G, Rootshield, TurfShield), or strain TH 35 (products known as ROOT PRO®) or strain TSTh20/PTA-0317 or strain 1295-22 (products known as Bio-Trek), and (2.22) *Beauveria brongniartii* (products known as Beaupro), (2.23) *Aschersonia aleyrodes*, (2.24) *Hirsutella thompsonii* (product known as Mycohit), (2.25) *Lagenidium giganteum* (products known as LAGINEX®), (2.26) *Metarhizium flavoviride*, (2.27) *Myrothecium verrucaria*, in particular strain strain AARC-0255 (product known as DiTera™), (2.28) *Pandora delphacis*, (2.29) *Tsukamurella paurometabola*, in particular strain C-924 (products known as HeberNem®), (2.29A) ARF 18 (Arkansas Fungus 18), (2.29B) *Glomus aggregatum*, (2.29C) *Glomus etunicatum*, (2.30) *Glomus intraradices*, (2.31) *Glomus mosseae*, (2.32) *Trichoderma atroviride*, in particular strain CNCM 1-1237 or strain NMI V08/002387, NMI V08/002389 or strain SKT-1/ FERM P-1651 or strain SKT-2/FERM P-16511 or strain SKT-3/FERM P-17021 (described in JP3691264)

or strain L52 (product known as SENTINEL®), (2.37) *Arthrobotrys dactyloides*, (2.38) *Arthrobotrys oligospora*, (2.39) *Arthrobotrys superba* (2.40) *Aspergillus flavus* strain NRRL 21882 (product known as AflaGuard®), (2.41) *Candida saitoana*, in particular strain NRRL Y-21022 (products known as BIOCURE® or BIOCOAT®), (2.42) *Chaetomium cupreum*, (2.43) *Chaetomium globosum*, (2.44) *Chondrostereum purpureum*, in particular strain PFC2139, (2.45) *Cladosporium cladosporioides* strain H39 (as described in EP2230918 A1), (2.46) *Conidiobolus obscurus*, (2.47) *Cryptococcus albidus* (product known as Yield Plus®.), (2.48) *Cryptococcus flavescens*, in particular strain NRRL Y-50378 and strain NRRL Y-50379, (2.49), *Dactylaria candida*, (2.50) *Entomophthora virulenta*, (2.51) *Harposporium anguillullae*, (2.52) *Hirsutella minnesotensis*, (2.53) *Hirsutella rhossiliensis*, (2.54) *Meristacrum asterospermum*, (2.55) *Microdochium dimerum*, (2.56) *Monacrosporium cionopagum*, (2.57) *Monacrosporium psychrophilum*, (2.58) *Monacrosporium drechsleri*, (2.59) *Monacrosporium gephyropagum*, (2.60) *Ophiostoma piliferum*, in particular strain D97 (products known as Sylvanex), (2.61) *Paecilomyces variotii*, in particular strain Q-09 (product known as Nemaquim), (2.62) *Pochonia chlamydosporia* (=*Vercillium chlamydosporiumi*), (2.63) *Pseudozyma aphidis*, (2.64) *Stagonospora heteroderae*, (2.65) *Stagonospora phaseoli*, (2.66) *Talaromyces flavus*, in particular strain V117b (products known as PROTUS®), (2.67) *Trichoderma viride* (also known as *Trichoderma gamsii*), in particular strain ICC 080 (products known as REMEDIER® WP, Bioderma®) and strain TV1 (products known as *T. viride* TV1, Agribiotec), (2.68) *Trichoderma harmatum*, isolate 382 (2.69) *Trichoderma koningii*, (2.70) *Trichoderma lignorum*, (2.71) *Trichoderma polysporum*, isolate IMI 206040 (ATCC 20476), (2.72) *Trichoderma stromaticum*, (2.73) *Trichoderma virens* (also known as *Gliocladium virens*), in particular strain GL-21 (products known as SOILGARD®), (2.74) *Ulocladium oudemansii*, in particular strain HRU3 (products known as BOTRY-ZEN®), (2.75) *Verticillium albo-atrum* in particular strain WCS850, (2.76) *Verticillium chlamydosporium*, (2.77) *Verticillium dahlia* isolate WCS 850 (products known as Dutch Trig), (2.78) *Zoophtora radicans*, (2.79) *Cylindrocarpon heteronema*, (2.80) *Exophiala jeanselmei*, (2.81) *Exophilia piscichila*, (2.82) *Fusarium aspergilus*, (2.83) *Fusarium oxysporum*, for example the non pathogenic strain Fo47 (product FUSACLEAN) or the non pathogenic strain 251/2RB (product known as BIOFOX®), (2.84) *Fusarium solani*, for example strain Fs-K (as described in patent application US20110059048), (2.85) *Gliocladium roseum*, (2.86) *Mucor haemelis* (products known as BIO-AVARD), (2.87) *Nematoctonus geogenius*, (2.88) *Nematoctonus leiosporus*, (2.89) *Phlebiopsis gigantea* (products known as ROTSOP®), (2.90) *Trichoderma album* (products known as Biozeid®), In one embodiment, from the given fungi and yeasts (2.1) to (2.90) or (2-1) to (2-31), the fungi and yeasts given under the numbers (2.10), (2.11), and (2.15) are to be used or employed in the present invention, in one embodiment in combination with compound (I-1-1), (I-1-2), as well as the mixtures (I-1-1)/(I-1-7), (I-1-2)/(I-1-8), optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.9) *Lecanicillium lecanii*, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.9a) *Lecanicillium lecanii* strain KV01, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.10) *Metarhizium anisopliae*, in particular strain F 52, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.11) *Metschnikovia fructicola*, in particular strain NRRL Y-30752, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.15a) *Paecilomyces lilacinus*, in particular spores of *P. lilacinus* strain 251, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (2.14) *Nomuraea rileyi*, optionally in the presence of an inoculant.

According to the invention biological control agents that are summarized under the term "protozoas" are:

(3.1) *Nosema locustae*, and (3.2) Vairimorpha.

It is preferred to use or employ in the present invention the compound (I-1-1), (I-1-2), as well as the mixtures (I-1-1)/(I-1-7), (I-1-2)/(I-1-8) in combination with (3.1) *Nosema locustae*, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (3.2) Vairimorpha, optionally in the presence of an inoculant.

According to the invention biological control agents that are summarized under the term "viruses" are:

(4.1) Gypsy moth (*Lymantria dispar*) nuclear polyhedrosis virus (NPV), (4.2) Tussock moth (Lymantriidae) NPV, (4.3) *Heliothis* NPV, (4.4) Neodiprion sertifer NPV (product known as Neocheck-S™, Virox), and (4.5) Codling moth (*Cydia pomonella*) granulosis virus (GV) (product known as Madex Plus), (4.6) Adoxophyes orana granulosis virus (product known as BIOFA-Capex®), (4.7) *Helicoverpa armigera* NPV (product known as ViVUS Max), (4.8) *Spodoptera exigua* NPV, (4.9) *Spodoptera littoralis* NPV, (4.10) *Spodoptera litura* NPV, (4.11) *Neodiprion abietis* NPV (product known as ABIETIV™).

It is preferred to use or employ in the present invention the compound (I-1-1), (I-1-2), as well as the mixtures (I-1-1)/(I-1-7), (I-1-2)/(I-1-8) in combination with (4.1) Gypsy moth nuclear polyhedrosis virus (NPV), optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (4.2) Tussock moth NPV, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (4.3) *Heliothis* NPV, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with 4.4 Neodiprion sertifer NPV, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (4.5) Codling moth granulosis virus (GV), optionally in the presence of an inoculant.

According to the invention biological control agents that are summarized under the term "entomopathogenic nematode" are:
(5.1) *Steinernema scapterisci*, (5.2) *Steinernema feltiae*, (5.3) *Steinernema carpocapsae*, (5.4) *Heterorhabditis heliothidis*, and (5.5) *Steinernema riobrave*, (5.6) *Steinernema glaseri*, (5.7) *Heterorhabditis bacteriophora*, (5.8) *Heterorhabditis baujardi*.

It is preferred to use or employ in the present invention the compound (I-1-1), (I-1-2), as well as the mixtures (I-1-1)/(I-1-7), (I-1-2)/(I-1-8) in combination with (5.1) *Steinernema scapterisci*, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (5.2) *Steinernema feltiae*, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (5.3) *Steinernema carpocapsae*, optionally in the presence of an inoculant.

It is preferred to use or employ in the present invention the compound (I-1-1), (I-1-2), as well as the mixtures (I-1-1)/(I-1-7), (I-1-2)/(I-1-8) in combination with (5.4) *Heterorhabditis heliothidis*, optionally in the presence of an inoculant.

Examples for inoculants which may be used or employed according to the invention are bacteria of the genus (6.1) *Rhizobium leguminosarum*, (6.2) *Rhizobium tropici*, (6.3) *Rhizobium loti*, (6.4) *Rhizobium trifolii*, (6.5) *Rhizobium meliloti*, (6.6) *Rhizobium fredii*, (6.7) *Azorhizobium caulinodans*, (6.8) *Pseudomonas*, (6.9) *Azospirillum*, (6.10) *Azotobacter*, (6.11) *Streptomyces*, (6.12) *Burkholdia*, (6.13) *Agrobacterium*, (6.14) Endo-Mycorhizza, (6.15) Ecto-Mycorhizza, (6.16) Vesicular-Arbuscular (VA) Mycorhizza, (6.17) *Bradyrhizobium*. It is preferred to use soil-inoculants.

According to the invention biological control agents that are summarized under the term "Botanical Extracs" are:
(7.1) *Thymus* oil (*Thymus vulgaris*), (7.2) *Cassia nigricans*, (7.3) *Quassia amara*, (7.4) Rotenon, (7.5) Garlic, (7.6) *Quillaja saponaria* (Nema-Q), (7.7) Sabadilla, in particular Veratrin, (7.8) Ryania, in particular Ryanodine, (7.9) Mistletoe (*Viscum album*), (7.10) common tansy (*Tanacetum vulgare*), (7.11) *Artemisia absinthium*, (7.12) *Urtica dioica*, (7.13) *Symphytum officinale*, (7.14) *Tropaeulum majus*, (7.15) *Quercus* (7.178) yellow mustard powder, (7.16) *Chenopodium anthelminticum*, (7.17) *Dryopteris filix-mas*, (7.18) bark of Chinese bittersweet (*Celastrus orbiculatus*), (7.191) *Equisetum arvense* (7.20) bark of *Celastus angulatus*, (7.21) Laminarin (Brown Algae), (7.22) Alginic acid (Brown Algae), (7.23) Chitin/Chitinosan, (7.24) *Chenopodium quinoa*, containing Saponine (product known as HeadsUp), (7.25) Sesame oil (product known as Dragongfire-CCPTM)

According to the invention biological control agents that are summarized under the term "products produced by microorganisms including proteins or secondary metabolites," are:

(8.1) Harpin protein, isolated from *Erwinia amylovora* (products known as Messenger, ProAct™, Employ™), (8.2) Thymol, The amount of the biological control agent selected from bacteria, in particular spore-forming bacteria, fungi or yeasts, protozoas, viruses, and entomopathogenic which is used or employed in combination with a compound of formula (I), preferably with a compound (I-1-1), (I-1-2), as well as the mixtures (I-1-1)/(I-1-7), (I-1-2)/(I-1-8), optionally in the presence of an inoculant, depends on the final formulation as well as size or type of the plant, plant parts, seeds, harvested fruits and vegetables to be treated. Usually, the biological control agent to be employed or used according to the invention is present in about 2% to about 80% (w/w), preferably in about 5% to about 75% (w/w), more preferably about 10% to about 70% (w/w) of its solo-formulation or combined-formulation with the compound of formula (I), and optionally the inoculant.

If bacteria, fungi or yeasts are selected as biological control agent, in particular those who are named as being preferred, namely (2.10), (2.11), and (2.15), it is preferred that they are present in a solo-formulation or the combined-formulation in a concentration in excess of $10^5$-$10^{12}$ cfu/g (colony forming units per gram), preferably in excess of $10^6$-$10^{11}$ cfu/g, more preferably $10^7$-$10^{16}$ cfu cfu/g and most preferably about $10^9$ cfu/g.

Also the amount of compound of formula (I) which is used or employed in combination with the biological control agent selected from bacteria, in particular spore-forming bacteria, fungi or yeasts, protozoas, viruses, entomopathogenic nematodes, and botanical extracts or products produced by microorganisms including proteins or secondary metabolites, optionally in the presence of an inoculant, depends on the final formulation as well as size or type of the plant, plant parts, seeds, harvested fruit or vegetable to be treated. Usually, the compound of formula (I) to be employed or used according to the invention is present in about 0.1% to about 80% (w/w), preferably 1% to about 60% (w/w), more preferably about 10% to about 50% (w/w) of its solo-formulation or combined-formulation with the biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant.

It is preferred to employ or use the compound of formula (I) and the biological control agent selected from bacteria, in particular spore-forming bacteria, fungi or yeasts, protozoas, viruses, entomopathogenic nematodes, and botanical extracts or products produced by microorganisms including proteins or secondary metabolites, and if present also the inoculant in an synergistic weight ratio. The skilled person is able to find out the synergistic weight ratios for the present invention by routine methods. The skilled person understands that these ratios refer to the ratio within a combined-formulation as well as to the calculative ratio of compound of formula (I) and the biological control agent described herein when both components are applied as mono-formulations to a plant to be treated. The skilled person can calculate this ratio by simple mathematics since the volume and the amount of compound of formula (I) and the biological control agent, respectively, in a mono-formulation is known to the skilled person. In one embodiment, the said ratio refer to the ratio of the both components after both components, i.e. compound of formula (I) and the biological control agent, respectively, were applied to a plant to be treated independently whether the components were applied to a plant to be treated in form of solo-applications or in form of a combined-formulation.

In particular, the synergistic weight ratio of the compound of formula (I) to the bacteria, in particular spore forming bacteria, as biological control agent lies in the range of 100:1 and 1:5000 (wt/wt), preferably in the range of 50:1 and 1:2500 (wt/wt). It has to be noted that before mentioned ratios ranges are based on a spore preparation of the bacterium which contains $10^9$-$10^{10}$ spores per gram. If spore preparations vary in density, the ratios have to be adapted accordingly to match the above listed ratio ranges. A ratio of 1:100 means 100 weight parts of the spore preparations of the spore forming bacteria to 1 weight part of the compound of formula (I).

In one preferred embodiment, when a biological control agent is *Bacillus subtilis*, preferably strain GB 03, the synergistic weight ratio of a compound of formula (I) to a preparation of *B. subtilis* of $10^{10}$ *B. subtilis* spores per gram preparation is between 100:1 and 1:500 or even between 10:1 and 1:200 such as between 5:1 and 1:50 or between 1:1 and 1:10.

In one preferred embodiment, when a biological control agent is *Bacillus amyloliquefaciens*, preferably strain FZB 42, the synergistic weight ratio of a compound of formula (I) to a preparation of *B. amyloliquefaciens* of $10^{10}$ *B. amyloliquefaciens* spores per gram preparation is between 100:1 and 1:5000 or even between 10:1 and 1:2500 such as between 5:1 and 1:500 or between 1:1 and 1:100.

In one preferred embodiment, when a biological control agent is *Bacillus pumilus*, preferably strain QST, the synergistic weight ratio of a compound of formula (I) to a preparation of *Bacillus pumilus* of $10^9$ *Bacillus pumilus* colony forming units (cfu) per gram preparation is between 100:1 and 1:5000 or even between 10:1 and 1:2500 such as between 5:1 and 1:500 or between 1:1 and 1:100.

In particular, the synergistic weight ratio of the compound of formula (I) to the fungi or yeasts lies in the range of 100:1 to 1:50.000, preferably in the range of 50:1 to 1:25.000. It has to be noted that before mentioned ratios ranges are based on a the spore preparation of the bacterium which contains $10^9$-$10^{10}$ spores (fungi) or cells (yeast) per gram. If spore preparations vary in density, the ratios have to be adapted accordingly to match the above listed ratio ranges. A ratio of 1:100 means 100 weight parts of the spore or cell preparation of the fungi or yeast to 1 weight part of the compound of formula (I)

In one preferred embodiment, when a biological control agent is *Metschnikowia fructicola*, preferably strain NRRL Y-30752, the synergistic weight ratio of a compound of formula (I) to a preparation of *M. fructicola* of $10^{10}$ *M. fructicola* cells per gram preparation is between 10:1 and 1:2500 or even between 1:1 and 1:1250 such as between 1:1 and 1:500 or between 1:1 and 1:200.

In another preferred embodiment, when a biological control agent is *Paecilomyces lilacinus*, preferably strain 251, the synergistic weight ratio of a compound (of formula (I) to a preparation of *P. lilacinus* of $10^{10}$ *P. lilacinus* spores per gram preparation is between 500:1 and 1:50000 or even between 100:1 and 1:25000 such as between 1:1 and 1:5000 or between 1:1 and 1:2500 or between 1:1 and 1:500 or between 1:1 and 1:100.

In another preferred embodiment, when a biological control agent is *Metarhizium anisopliae*, preferably strain F52, the synergistic weight ratio of a compound of formula (I) to a preparation of *M. anisopliae* of $10^9$ *M. anisopliae* spores per gram preparation is between 100:1 and 1:1000 or even between 10:1 and 1:200 such as between 1:1 and 1:100 or between 1:1 and 1:10.

In one embodiment of the present invention, a biological control agent is a fungus and the concentration of the fungus after dispersal is at least 50 g/ha, such as 50-7500 g/ha, 50-2500 g/ha, 50-1500 g/ha; at least 250 g/ha (hectare), at least 500 g/ha or at least 800 g/ha.

In one embodiment of the present invention, a biological control agent is a fungus, such as *Paecilomyces lilacinus*, e.g., strain 251, and the concentration of the fungus after dispersal is at least 50 g/ha; at least 100 g/ha; at least 1000 g/ha; at least 2500 g/ha, such as 2500-7500 g/ha, 2500-6000 g/ha; or at least 4000 g/ha, such as 4000-6000 g/ha.

In one embodiment of the present invention, a biological control agent is a fungus, such as *Metarhizium anisopliae*, e.g., strain F52 and the concentration of the fungus after dispersal is at least 50 g/ha, such as 50-7500 g/ha, 50-2500 g/ha, 50-250 g/ha; or at least 100 g/ha, such as 100 g/ha-1000 g/ha or 100-250 g/ha.

In one embodiment of the present invention, a biological control agent is yeast, such as *Metschnikowia fructicola*, and the concentration of the yeast after dispersal is at least 50 g/ha, such as 50-5000 g/ha, 50-2000 g/ha; at least 1000 g/ha; at least 1500 g/ha, such as 500-5000 g/ha, 500-2500 g/ha, 500-2000 g/ha.

In one embodiment of the present invention, a biological control agent is a bacterium and the concentration of the bacteria after dispersal is at least 50 g/ha, at least 100 g/ha or at least 150 g/ha.

In one embodiment of the present invention, a biological control agent is a bacterium, and the concentration of the bacteria after dispersal is at least 50 g/ha (hectare), such as 50-7500 g/ha, 50-2500 g/ha, 50-1500 g/ha; at least 250 g/ha; at least 100 g/ha, such as 100-5000 g/ha, 100-2500 g/ha, 100-1500 g/ha or 100-250 g/ha; or at least 800 g/ha, such as 800-5000 g/ha or 800-2500 g/ha.

In another embodiment of the present invention, a biological control agent is a bacterium, such as *B. subtilis*, e.g., strain GB 03, and the concentration of the bacteria after dispersal is at least 50 g/ha such as 50-5000 g/ha, 50-2500 g/ha, 50-200 g/ha; at least 100 g/ha, at least 500 g/ha, at least 800 g/ha, such as 800-5000 g/ha or 800-2500 g/ha.

In another embodiment of the present invention, a biological control agent is a bacterium, such as *B. amyloliquefaciens* and the concentration of the bacteria after dispersal is at least 500 g/ha, such as 500-5000 g/ha, 500-2500 g/ha.

In one embodiment of the present invention, a biological control agent is a virus and the concentration of the virus after dispersal is at least 50 g/ha such as 50-7500 g/ha, 50-2500 g/ha, 50-1500 g/ha; at least 100 g/ha or at least 150 g/ha.

In one embodiment of the present invention, a biological control agent is a virus, such as Codling moth (*Cydia pomonella*) granulosis virus and the concentration of the virus after dispersal is at least 50 g/ha (hectare) such as 50-5000 g/ha, 50-2500 g/ha, 50-1500 g/ha or 50-250 g/ha; or at least 100 g/ha, such as 100-500 g/ha or 100-250 g/ha.

In one embodiment of the present invention, a biological control agent is a nematode and the concentration of the nematodes is at least $10^6$ nematodes/ha, e.g., larval stage nematodes/ha, such as $10^6$-$10^{15}$ nematodes/ha, e.g., larval stage nematodes/ha, $10^6$-$10^{12}$ nematodes/ha, e.g., larval stage nematodes/ha, at least $10^8$ nematodes/ha, e.g., larval stage nematodes/ha such as $10^8$-$10^{15}$ nematodes/ha, e.g., larval stage nematodes/ha, $10^8$-$10^{12}$ nematodes/ha, e.g., larval stage nematodes/ha; or at least $10^9$ nematodes/ha, e.g., larval stage nematodes/ha, such as $10^9$-$10^{15}$ nematodes/ha, e.g., larval stage nematodes/ha or $10^9$-$10^{12}$ nematodes/ha, e.g., larval stage nematodes/ha.

In one embodiment of the present invention, the ratios between bacteria (such as *Bacillus amyloliquefaciens, Bacillus subtilis, Bacillus pumilus, Bacillus cereus*) and compound of formula (I) in a solo- or combined-formulation or on or in a plant to be treated or its surrounding, habitat or storage space is between 5000:1 to 1:125, between 2500:1 to 1:25 or even 500:1 to 1:5.

In one embodiment of the present invention, the ratios between fungi (such as *Metarhizium anisopliae, Paecilomyces lilacinus, Beauveria bassiana, Nomuraea rileyi*) and compound of formula (I) in a solo- or combined-formulation or on or in a plant to be treated or its surrounding, habitat or storage space is between 50000:1 to 1:125, between 25000:1 to 1:25 or even 500:1 to 1:5.

In one embodiment of the present invention, the ratios between yeast (such as *Metschnikowia fructicola*) and compound of formula (I) in a solo- or combined-formulation or on or in a plant to be treated or its surrounding, habitat or storage space is between 2500:1 to 1:125, between 1250:1 and 1:125 between 125:1 to 1:50, between 100:1 to 1:25 or even 50:1 to 1:5.

In one embodiment of the present invention, the ratios between nematodes (such as *Steinernema feltiae* and *Steinernema carpocapsae*) and compound of formula (I) in a solo- or combined-formulation or on or in a plant to be treated or its surrounding, habitat or storage space is between 125:1 to 1:125, between 100:1 to 1:25 or even 50:1 to 1:5.

The application rate of the biological control agent selected from bacteria, in particular spore-forming bacteria, fungi or yeasts, protozoas, viruses, entomopathogenic nematodes and botanical extracts to be employed or used according to the present invention may vary. The skilled person is able to find the appropriate application rate by way of routine experiments.

Microorganisms such as fungi or bacteria can be obtained by conventional fermentation processes. The fermentation can be carried out using solid, semi-solid or liquid nutrient media. If spores such as conidia are used, preference is given to solid or semi-solid nutrient media. The nutrient media contain the nutrients suitable and known for the cultivation of the respective microorganisms, in particular one or more metabolizable carbon sources or nitrogen sources and mineral salts. The fermentation is generally carried out at temperatures between about 3° and about 40° C., preferably between 20° and 35° C. For example, a representative fermentation is described in U.S. Pat. No. 5,804,208.

A fermentation process comprises in general the steps of a) incubating spores such as conidia of a microorganism in or on a nutrition medium (such as agar with further additives such as oatmeal); b) separating spores such as conidia from the nutrition medium after the incubation time, (e.g., by shake off the conidia from the medium, centrifuging, filtrating); and optionally c) preparing an emulsion of said isolated conidia.

The skilled person is well aware how to adapt fermentation to a given microorganism such as fungi or bacteria. In the following, several fermentations are exemplified in more detail. These examples are not meant to limit the scope of the present invention.

Fungi

The fungus *Metarhizium anisopliae*, strain DSM 3884, is known from EP-A-0268177. The production of conidia of *Metarhizium anisopliae* is exemplified in EP 0794704 B1 (U.S. Pat. No. 5,804,208).

A nutrition medium such as oatmeal agar (e.g., composition: 30 g of oat flakes and 20 g of agar) in a Petri dish was inoculated with, e.g., 3 week old conidia of the *Metarhizium anisopliae* strain DSM 3884. The incubation time to multiply the conidia is, e.g., 3, 4, 5, or 6 days. The incubation temperature can be around 7° C. to around 40° C., e.g. 22° to 25° C. The formed conidia was isolated by, e.g., shaking off the conidia. The conidia can be stirred with 50 ml of water containing 1% of a non-ionic emulsifier such as an emulsifier based on polyoxy-ethylene (20) sorbitan monolaurate (Tween 20®) until a suspension was obtained in which the conidia was present as isolated particles. The conidia titer was and can be determined using, e.g., a Neubauer chamber. The conidia can be stored in closed cases under dry conditions, preferably at temperatures between 0° and 25° C.

*Paecilomyces lilacinus* strain 251 was isolated from infected nematode eggs in the Philippines, and correctly described taxonomically in 1974. Optimal laboratory growth of *Paecilomyces lilacinus* strain 251 occurs at 21-27° C., and does not grow or survive above 36° C. (U.S. Environmental Protection Agency, *P. lilacinus* strain 251 Fact sheet). The following cultivation of *Paecilomyces lilacinus* is exemplified in Patent Application WO/1994/025579 (1994):

*Paecilomyces lilacinus* (Thorn) Samson (CBS 143.75), obtained e.g. from the CBS (Central Bureau of Fungal Cultures) in Baarn (The Netherlands), can be maintained on Potato Dextrose Agar (PDA; Difco laboratories) at 25° C. A conidial suspension was obtained by adding sterilized water (e.g., 5 ml) to a Petri dish containing sporulating mycelium and scraping the surface with a glass rod. Liquid cultures were obtained by inoculating conidia of the fungus to minimal salt medium or corn flour medium supplemented with the substrate. The minimal salt medium (MM) consists of 4.56 g H2PO4, 2.77 g KH2 HP04, 0.5 g MgS04.7H20 and 0.5 g KCI/l, pH 6.0. Mycelium can be obtained by centrifuging a, e.g., 6 day old culture of conidia of *Paecilomyces lilacinus*. For example, cultures can be grown in a shaking water bath for several days at 30° C. and 125 strokes per minute. Culture filtrates were obtained by centrifuging cultures for, e.g., 45 min at 9000 g.

The preparation of *Metschnikowia fructicola* is exemplified in U.S. Pat. No. 6,994,849:

The yeast species *Metschnikowia fructicola* was isolated from the surface of grape berries (cv. Superior) grown in the central part of Israel. At various stages, individual berries were submersed in sterile distilled water in 100 ml beakers and shaken vigorously for 2 hours on rotary shaker at 120 rpm. Aliquots of 100 ml were removed from the wash liquid and plated on PDA (Potato Dextrose Agar; DIFCO Laboratories, U.S.A.) medium. Following 4-5 days of incubation, yeast colonies were picked randomly according to colony characteristics (color and morphology) and streaked individually on fresh medium to obtain biologically pure cultures. Cultures were further purified by repeated streaking on PDA. Identification and characterization of the new species was done at the Microbial Genomics and Bioprocessing center, USDA-ARS, Peoria, Ill., USA. *Metschnikowia fructicola* was deposited at the NRRL under the number Y-30752. This deposit has been made in compliance with the terms of the Budapest Treaty.

*Metschnikowia fructicola* was propagated under aerobic conditions at temperatures ranging from 5° C. to 37° C. Optimal growth temperature is between 20° C. and 27° C. The yeast grows in liquid medium (nutrient broth; Droby et al., 1989) with a neutral pH. The cell density of the yeast generally reached its maximum (stationary stage) growth in 24-48 hours. For laboratory and small scale tests growth in Erlenmeyer flasks containing the medium and shaken on a rotary shaker was suitable. For large scale and commercial tests, fermentation tanks and industrial growth media were preferred. The yeast cells were harvested by centrifugation using conventional laboratory or industrial centrifuges.

Bacteria

The bacteria *Bacillus subtilis* is a naturally occurring bacteria found in soils all over the world. *Bacillus subtilis* strain QST713 was isolated in 1995 by AgraQuest Inc. from soil in a California peach orchard. This product is applied to foliage (NYDEC 2001). In contrast, *Bacillus subtilis* strain GB03 (Kodiak®) was discovered in Australia in the 1930's and is applied either as a seed treatment or directly to soil. Neither strain is considered a genetically modified organism (Cornell University: Organic Resource Guide, Material fact sheet—*Bacillus subtilis*)

Isolation of *Bacillus subtilis* and related strains from soil: To isolate wild *Bacillus subtilis* strains, e.g., 2 g soil samples were dissolved in 2 ml of 10 mM Tris/HCl (pH 7.2) and then boiled at 95° C. for 5 min. From these samples, 0.1 ml of each sample was then spread onto LB plates and incubated at 37° C.

Sporulation assay: *Bacillus subtilis* strains were grown in 26 SG medium at 37° C. and sporulation was assayed at 24 hours after the end of the exponential phase. The number of spores per ml culture was determined by identifying the number of heat-resistant colony forming units (80° C. for 10 min) on LB plates.

*Bacillus subtilis*, strain Marburg, was grown aerobically in heart infusion broth (Difco Laboratories, Detroit, Mich.) on shaker at about 37° C. From an overnight culture 4 drops were inoculated into 70 ml of pre warmed broth. Growth was measured as optical density at 620 nm. Cells were collected after 3.5-4.5 hours in the exponential phase of growth. Centrifugation was carried out at room temperature for 15 min at 7000 g (The Journal of Cell Biology. Volume 48, 1971 • pages 219-224).

*Bacillus subtilis* is active in temperatures between 7° C. and 45° C.

*Bacillus amyloliquefaciens* strain FZB42, was originally isolated from infested soil in Germany (Krebs et al., 1998, Chen et al., 2007). *Bacillus amyloliquefaciens* strain FZB42 was cultivated in Luria broth (LB—1% w/v peptone, 0.5% w/v yeast extract, 0.5% w/v NaCL) at 30° C. (Journal of Biotechnology 151 (2011) 303-311). The bacteria was grown in Landy medium as described in Koumoutsi et al., 2004. To prepare surface cultures, the strains were grown in petri dishes containing 1.5% Landy agar for 24 h at 37° C. and stored at room temperature prior to MALDI-TOF-MS analysis. Fermentation in liquid media was carried out in flasks at 30° C. and 180 rpm in a shaker (Journal of Bacteriology, February 2004, p. 1084-1096).

Viruses

*Cydia pomonella* granulosis viruses (CpGV) which are used in the products MADEX (Andermatt Biocontrol) and Granupom (Probis GmbH) are deposited since 2005 at the German Collection of Microorganisms and Cell Cultures (DSMZ). Isolates used for the production of MADEX (Andermatt Biocontrol), Granupom (Probis GmbH), VIRGO (SipcamS.p.A.) and CARPOVIRUSINE (Arysta Life-Science S.A.S) were all derived from the Mexican isolate originally isolated in 1963 and are not genetically modified. (Virus accession number: GV-0001)

The identity of the virus produce can be bioanalytically checked against the parent strain by SDS-polyacrylamide-gel electrophoresis of the virus protein sand by Restriction endonuclease analysis of viral DNA.

Prior to DNA isolation the test item has to be purified. The purified CpGV OB pellet is resuspended in 1 ml sterile water and the CpGV OB concentration is enumerated in the Petroff-Hausser counting chamber. The concentration of active *Cydia pomonella* Granulosis virus (CpGV) is determined by means of a quantitative bioassay. The granules (occlusion bodies) of CpGV are counted under the light microscope. The virus titer in the end-use product is adjusted to the requested granules/l (Assessment Report: *Cydia pomonella* Granulovirus (CpGV)—Mexican Isolate (2007).

CpGV derives from the Mexican isolate of CpGV (Tanada, 1964) and is propagated in larvae of *Cydia pomonella*. Infected larvae are homogenized and centrifuged in 50% sucrose (w/w). The pellet is resuspended and the granules are purified by, e.g., centrifugation through a linear 50% to 60% (w/w) sucrose gradient, generating a virus band which is then repeatedly washed in Tris buffer and pelleted to remove residual sucrose. (Journal of general virology (1992), 73, 1621-1626).

Entomopathogenic Nematodes

Nematodes can be reared in liquid culture techniques (see, e.g., U.S. Pat. No. 5,023,183 which is herewith incorporated by reference in its entirety) and stored, for example, as eggs, larvae in suspension cultures or in clay powder or adult nematodes, e.g., in clay powder. Nematodes can be held in the refrigerator (2-6° C.) until use for up to 4 weeks and can be reactivated by suspension in warm water (>12° C.).

One method to isolate entomopathogenic nematodes from soil is described by Cairns, 1960, *Folia parasitica* 47: 315-318, 2000. For soil samples, a sieving-decanting method was employed with final isolation of the nematodes from the sieving debris using a Baermann funnel with cotton filter. For this method, which is commonly applied for the extraction of plant-parasitic and soil nematodes (Southey 1986), 250 ml soil was used. The nematode suspension was fixed, checked for the presence of entomopathogenic nematodes using an inverted light microscope, and the number of *Steinernema* specimens was determined. Species identification was mostly done at high microscopical magnification using morphological characters of the infective-stage juveniles (Sturhan in Hominick et al. 1997, and unpublished).

Entomopathogenic nematodes can be mass-produced by in-vivo or in-vitro methods. Larvae of *Galleria mellonella* are most commonly used to rear nematodes because of their commercial availability. Several researchers (Dutky et al. 1964, Howell 1979, Lindegren et al. 1993, Flanders et al. 1996) have described the methods of nematode infection, inoculation, and harvesting. Using the in-vivo process, yields between $0.5 \times 10^5$-$4 \times 10^5$ infective juveniles, depending on the nematode species, have been obtained. During the past few years a distinct cottage industry has emerged in the USA which utilizes the in-vivo process for nematode mass-production for sale, especially in the home lawn and garden markets. The in-vivo process, however, lacks any economy of scale; the labor, equipment, and material (insect) costs increase as a linear function of production capacity. Perhaps even more important is the lack of improved quality while increasing scale. The in-vivo nematode production is increasingly sensitive to biological variations and catastrophes as scale increases (Friedman 1990). Several formulations have been developed for the storage and application of entomopathogenic nematodes. The shelf life of different nematode-based products varies depending on the formulation, nematode species and temperature. In the simplest type of formulation, the nematodes are impregnated onto moist carrier substrates providing substantial interstitial spaces leading to increased gas exchange. Such carriers include polyether polyurethane sponge, cedar shavings, peat, vermiculite, etc. Nematodes held on the sponge need to be hand-squeezed into water before application, whereas from the other carriers they may be applied directly to the soil as mulch (Neotropical Entomology, vol. 30, no. 2, Londrina, June 2001, ISSN 1519-566X).

A bioassay to determine nematode viability is described, e.g., in Simser (J. of Nematology 24(3):374-378; 1992). The Nematode viability was verified by host bioassay. Late instar larvae of the greater wax moth, *Galleria mellone*, were buried 2.5 cm deep between plants before nematode application (four larvae per replicate), collected after 7 days, placed in petri dishes (9 cm diameter) and held in darkness at ca. 25 C. Insect mortality (>90%) and subsequent nematode propagation with cadavers demonstrated infectivity of the nematodes. The skilled person is well aware how to adopt this kind of bioassay to different nematode species.

The preferred application rate of bacteria as biological control agent, in particular of spores of the bacteria (1.26a), namely *B. subtilis* strain GBO3, lies in the range of 0.1 to 3 kg/ha.

The preferred application rate of fungi as biological control agent, in particular the fungi *Metarhizium anisopliae* strain F 52 lies in the range of 0.1 to 3 kg/ha The preferred application rate of yeasts as biological control agent, in particular the yeast *Metschnikowia fructicola* strain NRRL Y-30752 lies in the range of 0.05 to 8 kg/ha.

The preferred application rate of protozoa, viruses, and entomopathogenic nematodes as biological control agents lies in the range of 0.5 to 10 kg/ha.

It is generally preferred to use or employ the compound of formula (I) and the biological control agent selected from bacteria, in particular spore-forming bacteria, fungi or yeasts, protozoas, viruses, and entomopathogenic nematodes, and if applicable also the inoculant on horticultural crops, such as cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Poaceae* sp. (for example sugarcane), *Asteraceae* sp. (for example sunflowers), *Brassicaceae* sp. (for example white cabbage, red cabbage, broccoli, cauliflowers, Brussels sprouts, pak choi, turnip cabbage, garden radish, and also oilseed rape, mustard, horseradish and cress), *Fabacae* sp. (for example beans, peas, peanuts), *Papilionaceae* sp. (for example soya beans), *Solanaceae* sp. (for example potatoes), *Chenopodiaceae* sp. (for example sugar beet, fodder beet, Swiss chard, beetroot); crop plants and ornamental plants in garden and forest; and also in each case genetically modified varieties of these plants.

Horticultural crops particularly includes carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, turnip cabbage, kale, radish, rutabaga, turnip, asparagus, bean, pea, apples, raspberry, strawberry, banana, mango, grapes, peaches, pears, guava, pineapple, pomegranate, garlic, capsicum, chili, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, cantaloupes and includes their harvested goods, such as fruits and vegetables.

It is further generally preferred to use or employ the compound of formula (I) and the biological control agent selected from bacteria, in particular spore-forming bacteria, fungi or yeasts, protozoas, viruses, and entomopathogenic nematodes, and if applicable also the inoculant on broad acre crops, such as cotton, corn, soybean, cereals, canola, oil seed rape, sugar cane and rice.

Agrochemical formulations as mentioned herein, in particular solo-formulations and combined-formulations may generally include carrier, which is be understood as meaning a natural or synthetic, organic or inorganic substance which is mixed or combined with the active compounds for better applicability, in particular for application to plants or plant parts or seeds. The carrier which may be solid or liquid is generally inert and should be suitable for agricultural use. The formulations mentioned can be prepared in a manner known per se, for example by mixing the active the compound of formula (I) and the biological control agent selected from bacteria, in particular spore-forming bacteria, fungi or yeasts, protozoas, viruses, and entomopathogenic nematodes, and if applicable also the inoculant with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

Moreover, agrochemical formulations as mentioned herein may also generally include suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Moreover, agrochemical formulations as mentioned herein may also generally include suitable liquefied gaseous extenders or carriers are liquids which are gaseous at ambient temperature and under atmospheric pressure, for example aerosol propellants, such as butane, propane, nitrogen and carbon dioxide.

Moreover, agrochemical formulations as mentioned herein may also generally include suitable tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

Moreover, agrochemical formulations as mentioned herein may also generally include extender. If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

In one embodiment, an agrochemical formulation such as a solo-formulation or a combined-formulation comprises at least one of the following solvents selected from the group consisting of water, ketones, such as acetone, dimethylformamide and dimethyl sulphoxide.

In a further embodiment, an agrochemical formulation such as a solo-formulation or a combined-formulation comprises at least one of the following solvents selected from the group consisting of water, ketones, such as acetone, dimethylformamide and dimethyl sulphoxide; and further comprises an emulsifier selected from the group consisting of alkylaryl polyglycolether.

Moreover, agrochemical formulations as mentioned herein may also generally include additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention. It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

Moreover, agrochemical formulations as mentioned herein may also generally include other additional components, for example protective colloids, binders, adhesives, thickeners, thixotropic substances, penetrants, stabilizers, sequestering agents, complex formers.

Agrochemical formulations as mentioned herein can be used in form of aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The combinations according to the invention do not only comprise ready-to-use formulations which can be applied with suitable apparatus to the plant or the seed, but also commercial concentrates which have to be diluted with water prior to use.

It is preferred that the composition containing a compound of formula (I) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally an inoculant according to the invention is formulated in a single, stable solution, or emulsion, or suspension. For solutions, the compound of formula (I) is dissolved in a suitable solvent before the biological control agent is added.

Suitable solvents are liquid and include petroleum based aromatics, such as xylene, toluene or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsions and suspensions, the solvent is water.

In one embodiment, the compound of formula (I) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, are suspended in separate solvents and mixed at the time of application.

In a preferred embodiment the compound of formula (I) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant are combined in a ready-to-use formulation that exhibits a shelf-life of at least two years. In use, the liquid can be sprayed or atomized foliarly or in-furrow at the time of planting the plant. The liquid composition can be introduced to the soil before germination of the seed or directly to the soil in contact with the roots by utilizing a variety of techniques including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

In some embodiments, the terms alkane, alkyl, alkene, alkenyl, alkine, alkinyl, aryl when mentioned herein refer to groups containing $C_1$-$C_{20}$, $C_1$-$C_8$ or $C_1$-$C_6$ carbon atoms. Similarly, heteroaryl and other functional groups comprising alkyl, alkenyl, alkinyl or aryl, such as ketones, ethers, amines, etc., may contain $C_1$-$C_{20}$, $C_1$-$C_8$ or $C_1$-$C_6$ carbon atoms. Of course, combinations which are contrary to the law of nature (e.g., $C_2$-aryl) are excluded. The skilled person is well aware which combinations have to be excluded based on his or her expertise. In some embodiments, the term "poly" refers to units of 2-50000, 2-5000, 2-500, 2-50, 5-500, 50-500, 5-50 subunits.

In the agrochemical formulations or in the use forms of the compound of formula (I) and the biological control agent selected from bacteria, in particular spore-forming bacteria, fungi or yeasts, protozoas, viruses, entomopathogenic nematodes, and botanical extracts or products produced by microorganisms including proteins or secondary metabolites, and or the inoculant, there may be additionally at least one further active compound present. Such active compounds may be insecticides, attractants, sterilants, bactericides, acaricides, nematicides, fungicides, growth regulators, herbicides, fertilizers, safeners and semiochemicals. In one embodiment, the solid or liquid agrochemical formulations or use forms as mentioned before, may further contain functional agents capable of protecting seeds from the harmful effects of selective herbicides such as activated carbon, nutrients (fertilizers), and other agents capable of improving the germination and quality of the products or a combination thereof.

Conventional seeds which can be treated according to the invention are seeds of any plant variety employed in agriculture, in the greenhouse, in forests or in horticulture or in vineyards and include horticultural and broad acre crops. In particular, this takes the form of seed of cereals (such as wheat, barley, rye, triticale, millet, oats), maize (corn), cotton, soybean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cotton, soybean, rape, cereals (such as wheat, barley, rye, triticale, and oats), maize (corn), beets, potatoes and rice is of particular importance.

Transgenic seeds containing at least one heterologous gene which allows the expression of a polypeptide or protein having insecticidal properties are particularly preferred to be treated according to the invention. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

The compounds of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant according to the invention are preferably formulated as a solo-agrochemical formulation or a combined-agrochemical formulation with the aim to be sufficiently stable so that the treatment of the plants, plant parts, seeds, harvested fruits and vegetables does not cause any damage.

However, the compounds of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant can also be applied directly, that is to say without comprising further components and without having been diluted.

In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the compound of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant is applied to the seed and/or the amount of further additives is chosen in such a way that the germination of the seed is not adversely affected, or that the resulting plant is not damaged.

Agrochemical formulations for treating seeds (seed dressing formulations) according to the invention are solutions, emulsions, suspensions, powders, foams, slurries or other coating materials for seed, and also ULV formulations (cf. U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2).

Such seed dressing formulations are prepared in a known manner by mixing the compound of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof.

Preservatives that may be present in the seed dressing formulation include all compounds which can be used for such purposes in agrochemical compositions. By way of example, mention may be made of dichlorophen and benzyl alcohol hemiformal.

Secondary thickeners that may be present in the seed dressing formulations include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations are preferably the gibberellins A1, A3 (=gibberellic acid), A4 and A7; particular preference is given to using gibberellic acid. The gibberellins are known (cf. R. Wegler "Chemie der Pflanzenschutz— und Schädlingsbekämpfungsmittel" [Chemistry of Crop Protection Agents and Pesticides], Vol. 2, Springer Verlag, 1970, pp. 401-412).

The seed dressing formulations can be used directly or after dilution with water beforehand to treat seed of any of a very wide variety of types or transgenic plants. When the latter seeds are used, synergistic effects may also arise in interaction with the substances formed by expression.

Suitable mixing equipment for treating seed with the seed dressing formulations or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

According to the present invention, the seeds are substantially uniformly coated with one or more layers of the compound of formula (I), preferably compound (I-1-1), (I-1-2), as well as the mixtures (I-1-1)/(I-1-7), (I-1-2)/(I-1-8) and/or the at least one biological control agent selected from bacteria, in particular spore-forming bacteria, fungi or yeasts, protozoas, viruses, entomopathogenic nematodes and botanical extracts, or products produced by microorganisms including proteins or secondary metabolites, and optionally the inoculant using conventional methods of mixing, spraying or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and drying. The seeds can be primed or unprimed before coating with the compound of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant to increase the uniformity of germination and emergence. In an alternative embodiment, a dry powder formulation can be metered onto the moving seed and allowed to mix until completely distributed.

The seeds may be coated via a batch or continuous coating process. In a continuous coating embodiment, continuous flow equipment simultaneously meters both the seed flow and the seed treatment products. A slide gate, cone and orifice, seed wheel, or weighing device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating embodiment, batch treating equipment weighs out a prescribed amount of seed and places the seed into a closed treating chamber or bowl where the corresponding dose of seed treatment is then applied. This batch is then dumped out of the treating chamber in preparation for the treatment of the next batch. With computer control systems, this batch process is automated enabling it to continuously repeat the batch treating process.

In either embodiment, the seed coating machinery can optionally be operated by a programmable logic controller that allows various equipments to be started and stopped without employee intervention. The components of this system are commercially available through several sources such as Gustafson Equipment of Shakopee, Minn.

If planted, any plant seed capable of germinating to form a plant that is susceptible to attack by insects, nematodes and/or pathogenic fungi can be treated in accordance with the invention. Particularly suitable convential (i.e. not being a transgenic seeds) or transgenic seeds are those of cole crops, vegetables (in particular the vegetables as mentioned herein as being horticultural crops), fruits (in particular the vegetables as mentioned herein as being horticultural crops), trees, fiber crops, oil crops, tuber crops, coffee, flowers, legume, cereals, as well as other plants of the monocotyledonous and dicotyledonous species. Preference is given to seeds of horticultural crops and of broad acre crops as mentioned herein. In particular, among those crops, seeds to be coated include soybean, cotton, corn, peanut, tobacco, grasses, wheat, barley, rye, sorghum, rice, rapeseed, sugar beet, sunflower, tomato, pepper, bean, lettuce, potato, and carrot seeds.

Additionally, if the seed treatment is done with transgenic seeds, then the plants emerging from these seeds are capable of the expression of a protein directed against pests and pathogens. By treatment of such seed with the compound of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant certain pests and/or phytopathogens can already be controlled by expression of the, for example, insecticidal protein, and it is additionally surprising that a synergistic activity supplementation occurs when the compound of formula (I) and the biological control agents are used or employed for seed treatment, thereby improving still further the effectiveness of the protection from pest and pathogen infestation.

The agricultural pests and pathogens to be controlled when the compound of formula (I) and the biological control agents are used or employed according to the invention are given hereafter:

Agricultural Pests:
pests from the phylum Arthropoda, especially from the class Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia graminum*, *Bryobia praetiosa*, *Centruroides* spp., *Chorioptes* spp., *Dermanyssus gallinae*, *Dermatophagoides pteronyssinus*, *Dermatophagoides farinae*, *Dermacentor* spp., *Eotetranychus* spp., *Epitrimerus pyri*, *Eutetranychus* spp., *Eriophyes* spp., *Glycyphagus domesticus*, *Halotydeus destructor*, *Hemitarsonemus* spp., *Hyalomma* spp., *Ixodes* spp., *Latrodectus* spp., *Loxosceles* spp., *Metatetranychus* spp., *Neutrombicula autumnalis*, *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Steneotarsonemus* spp., *Steneotarsonemus spinki*, *Tarsonemus* spp., *Tetranychus* spp., *Trombicula alfreddugesi*, *Vaejovis* spp., *Vasates lycopersici*;
from the class Chilopoda, for example, *Geophilus* spp., *Scutigera* spp.;
from the order or the class Collembola, for example, *Onychiurus armatus*;
from the class Diplopoda, for example, *Blaniulus guttulatus*;
from the class Insecta, e.g. from the order Blattodea, for example, *Blattella asahinai*, *Blattella germanica*, *Blatta orientalis*, *Leucophaea maderae*, *Panchlora* spp., *Parcoblatta* spp., *Periplaneta* spp., *Supella longipalpa*;
from the order Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptolestes ferrugineus*, *Cryptorhynchus lapathi*, *Cylindrocopturus* spp., *Dermestes* spp., *Diabrotica* spp., *Dichocrocis* spp., *Dicladispa armigera*, *Diloboderus* spp., *Epilachna* spp., *Epitrix* spp., *Faustinus* spp., *Gibbium psylloides*, *Gnathocerus cornutus*, *Hellula undalis*, *Heteronychus arator*, *Heteronyx* spp., *Hylamorpha elegans*, *Hylotrupes bajulus*, *Hypera postica*, *Hypomeces squamosus*, *Hypothenemus* spp., *Lachnosterna consanguinea*, *Lasioderma serricome*, *Latheticus oryzae*, *Lathridius* spp., *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Necrobia* spp., *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllophaga helleri*, *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sitophilus oryzae*, *Sphenophorus* spp., *Stegobium paniceum*, *Sternechus* spp., *Symphyletes* spp., *Tanymecus* spp., *Tenebrio molitor*, *Tenebrioides mauretanicus*, *Tribolium* spp., *Trogoderma* spp., *Tychius* spp., *Xylotrechus* spp., *Zabrus* spp.;
from the order Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Calliphora vicina*, *Ceratitis capitata*, *Chironomus* spp., *Chrysomyia* spp., *Chrysops* spp., *Chrysozona pluvialis*, *Cochliomyia* spp., *Contarinia* spp., *Cordylobia anthropophaga*, *Cricotopus sylvestris*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hydrellia griseola*, *Hylemya* spp., *Hippobosca* spp., *Hypoderma* spp., *Liriomyza* spp., *Lucilia* spp., *Lutzomyia* spp., *Mansonia* spp., *Musca* spp., *Oestrus* spp., *Oscinella frit*, *Paratanytarsus* spp., *Paralauterborniella subcincta*, *Pegomyia* spp., *Phlebotomus* spp., *Phorbia* spp., *Phormia* spp., *Piophila casei*, *Prodiplosis* spp., *Psila rosae*, *Rhagoletis* spp., *Sarcophaga* spp., *Simulium* spp., *Stomoxys* spp., *Tabanus* spp., *Tetanops* spp., *Tipula* spp.;
from the order Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptocorisa varicornis*, *Leptoglossus phyllopus*, *Lygus* spp., *Macropes excavatus*, *Miridae*, *Monalonion atratum*, *Nezara* spp.,

*Oebalus* spp., Pentomidae, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order Homoptera, for example, *Acizzia acaciaebaileyanae*, *Acizzia dodonaeae*, *Acizzia uncatoides*, *Acrida turrita*, *Acyrthosipon* spp., *Acrogonia* spp., *Aeneolamia* spp., *Agonoscena* spp., *Aleyrodes proletella*, *Aleurolobus barodensis*, *Aleurothrixus floccosus*, *Allocaridara malayensis*, *Amrasca* spp., *Anuraphis cardui*, *Aonidiella* spp., *Aphanostigma pini*, *Aphis* spp., *Arboridia apicalis*, *Arytainilla* spp., *Aspidiella* spp., *Aspidiotus* spp., *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., *Calligypona marginata*, *Carneocephala fulgida*, *Ceratovacuna lanigera*, Cercopidae, *Ceroplastes* spp., *Chaetosiphon fragaefolii*, *Chionaspis tegalensis*, *Chlorita onukii*, *Chondracris rosea*, *Chromaphis juglandicola*, *Chrysomphalus ficus*, *Cicadulina mbila*, *Coccomytilus halli*, *Coccus* spp., *Cryptomyzus ribis*, *Cryptoneossa* spp., *Ctenarytaina* spp., *Dalbulus* spp., *Dialeurodes citri*, *Diaphorina citri*, *Diaspis* spp., *Drosicha* spp., *Dysaphis* spp., *Dysmicoccus* spp., *Empoasca* spp., *Eriosoma* spp., *Erythroneura* spp., *Eucalyptolyma* spp., *Euphyllura* spp., *Euscelis bilobatus*, *Ferrisia* spp., *Geococcus coffeae*, *Glycaspis* spp., *Heteropsylla cubana*, *Heteropsylla spinulosa*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Macrosteles facifrons*, *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Prosopidopsylla flava*, *Protopulvinaria pyriformis*, *Pseudaulacaspis pentagona*, *Pseudococcus* spp., *Psyllopsis* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoideus titanus*, *Schizaphis graminum*, *Selenaspidus articulatus*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*, *Zygina* spp.;

from the order Hymenoptera, for example, *Acromyrmex* spp., *Athalia* spp., *Atta* spp., *Diprion* spp., *Hoplocampa* spp., *Lasius* spp., *Monomorium pharaonis*, *Sirex* spp., *Solenopsis invicta*, *Tapinoma* spp., *Urocerus* spp., *Vespa* spp., *Xeris* spp.;

from the order Isopoda, for example, *Armadillidium vulgare*, *Oniscus asellus*, *Porcellio scaber*;

from the order Isoptera, for example, *Coptotermes* spp., *Cornitermes cumulans*, *Cryptotermes* spp., *Incisitermes* spp., *Microtermes obesi*, *Odontotermes* spp., *Reticulitermes* spp.;

from the order Lepidoptera, for example, *Achroia grisella*, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., *Choristoneura* spp., *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamstra brassicae*, *Melanitis leda*, *Mocis* spp., *Monopis obviella*, *Mythimna separata*, *Nemapogon cloacellus*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudaletia unipuncta*, *Pseudoplusia includens*, *Pyrausta nubilalis*, *Rachiplusia nu*, *Schoenobius* spp., *Scirpophaga* spp., *Scirpophaga innotata*, *Scotia segetum*, *Sesamia* spp., *Sesamia inferens*, *Sparganothis* spp., *Spodoptera* spp., *Spodoptera praefica*, *Stathmopoda* spp., *Stomopteryx subsecivella*, *Synanthedon* spp., *Tecia solanivora*, *Thermesia gemmatalis*, *Tinea cloacella*, *Tinea pellionella*, *Tineola bisselliella*, *Tortrix* spp., *Trichophaga tapetzella*, *Trichoplusia* spp., *Tryporyza incertulas*, *Tuta absoluta*, *Virachola* spp.;

from the order Orthoptera or Saltatoria, for example, *Acheta domesticus*, *Dichroplus* spp., *Gryllotalpa* spp., *Hieroglyphus* spp., *Locusta* spp., *Melanoplus* spp., *Schistocerca gregaria;* from the order Phthiraptera, for example, *Damalinia* spp., *Haematopinus* spp., *Linognathus* spp., *Pediculus* spp., *Ptirus pubis*, *Trichodectes* spp.;

from the order Psocoptera for example *Lepinatus* spp., *Liposcelis* spp.;

from the order Siphonaptera, for example, *Ceratophyllus* spp., *Ctenocephalides* spp., *Pulex irritans*, *Tunga penetrans*, *Xenopsylla cheopsis;* from the order Thysanoptera, for example, *Anaphothrips obscurus*, *Baliothrips biformis*, *Drepanothrips reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamomi*, *Thrips* spp.;

from the order Zygentoma (=Thysanura), for example, *Ctenolepisma* spp., *Lepisma saccharina*, *Lepismodes inquilinus*, *Thermobia domestica;* from the class Symphyla, for example, *Scutigerella* spp.;

pests from the phylum Mollusca, especially from the class Bivalvia, for example, *Dreissena* spp., and from the class Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.;

animal pests from the phylums Plathelminthes and Nematoda, for example, *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* phytoparasitic pests from the phylum Nematoda, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp., *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp., *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp.

It is furthermore possible to control organisms from the subphylum Protozoa, especially from the order Coccidia, such as *Eimeria* spp.

Some phytopathogens of fungal diseases which can be treated according to the invention may be mentioned by way of example, but not by way of limitation:

Diseases caused by powdery mildew pathogens, such as, for example, *Blumeria* species, such as, for example, *Blumeria graminis; Podosphaera* species, such as, for example, *Podosphaera leucotricha; Sphaerotheca* species, such as, for example, *Sphaerotheca fuliginea; Uncinula* species, such as, for example, *Uncinula necator;*

Diseases caused by rust disease pathogens, such as, for example, *Gymnosporangium* species, such as, for example, *Gymnosporangium sabinae; Hemileia* species, such as, for example, *Hemileia vastatrix; Phakopsora* species, such as, for example, *Phakopsora pachyrhizi* and *Phakopsora meibomiae; Puccinia* species, such as, for example, *Puccinia recondita* or *Puccinia triticina; Uromyces* species, such as, for example, *Uromyces appendiculatus;*

Diseases caused by pathogens from the group of the Oomycetes, such as, for example, *Albugo* species, such as, for example, *Albugo candida; Bremia* species, such as, for example, *Bremia lactucae; Peronospora* species, such as, for example, *Peronospora pisi* or *P. brassicae; Phytophthora* species, such as, for example *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum;*

Leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus* (conidia form: *Drechslera,* Syn: *Helminthosporium*) and *Cochliobolus miyabeanus; Colletotrichum* species, such as, for example, *Colletotrichum lindemuthianum; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans* and *Leptosphaeria nodorum; Magnaporthe* species, such as, for example, *Magnaporthe grisea; Microdochium* species, such as, for example, *Microdochium nivale; Mycosphaerella* species, such as, for example, *Mycosphaerella graminicola, Mycosphaerella arachidicola* and *Mycosphaerella fijiensis; Phaeosphaeria* species, such as, for example, *Phaeosphaeria nodorum; Pyrenophora* species, such as, for example, *Pyrenophora teres* and *Pyrenophora tritici repentis; Ramularia* species, such as, for example, *Ramularia collo-cygni* and *Ramularia areola; Rhynchosporium* species, such as, for example, *Rhynchosporium secalis; Septoria* species, such as, for example, *Septoria apii* and *Septoria lycopersici; Typhula* species, such as, for example, *Typhula incarnata; Venturia* species, such as, for example, *Venturia inaequalis;*

Root, sheath and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Sarocladium* species, such as, for example, *Sarocladium oryzae; Sclerotium* species, such as, for example, *Sclerotium oryzae; Tapesia* species, such as, for example, *Tapesia acuformis; Thielaviopsis* species, such as, for example, *Thielaviopsis basicola;*

Ear and panicle diseases (including maize cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as for example, *Septoria nodorum;*

Seed- and soil-borne decay, mould, wilt, rot and damping-off diseases, caused, for example, by *Alternaria* diseases caused for example by *Alternaria brassicicola; Aphanomyces* diseases caused for example by *Aphanomyces euteiches; Ascochyta* diseases caused for example by *Ascochyta lentis*; *Aspergillus* diseases caused for example by *Aspergillus flavus*; *Cladosporium* diseases caused for example by *Cladosporium herbarum*; *Cochliobolus* diseases caused for example by *Cochliobolus sativus*; (Conidiaform: *Drechslera, Bipolaris* Syn: *Helminthosporium*); *Colletotrichum* diseases caused for example by *Colletotrichum coccodes*; *Fusarium* diseases caused for example by *Fusarium culmorum*; *Gibberella* diseases caused for example by *Gibberella zeae*; *Macrophomina* diseases caused for example by *Macrophomina phaseolina*; *Microdochium* diseases caused for example by *Microdochium nivale*; *Monographella* diseases caused for example by *Monographella nivalis*; *Penicillium* diseases caused for example by *Penicillium expansum*; *Phoma* diseases caused for example by *Phoma lingam*; *Phomopsis* diseases caused for example by *Phomopsis sojae*; *Phytophthora* diseases caused for example by *Phytophthora cactorum*; *Pyrenophora* diseases caused for example by *Pyrenophora graminea*; *Pyricularia* diseases caused for example by *Pyricularia oryzae*; *Pythium* diseases caused for example by *Pythium ultimum*; *Rhizoctonia* diseases caused for example by *Rhizoctonia solani*; *Rhizopus* diseases caused for example by *Rhizopus oryzae*; *Sclerotium* diseases caused for example by *Sclerotium rolfsii*; *Septoria* diseases caused for example by *Septoria nodorum*; *Typhula* diseases caused for example by *Typhula incarnata*; *Verticillium* diseases caused for example by *Verticillium dahliae*;

Diseases caused by smut and bunt fungi, such as, for example, *Sphacelotheca* species, such as, for example, *Sphacelotheca reiliana*; *Tilletia* species, such as, for example, *Tilletia caries*; *Tilletia controversa*; *Urocystis* species, such as, for example, *Urocystis occulta*; *Ustilago* species, such as, for example, *Ustilago nuda*; *Ustilago nuda tritici*;

Fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *Penicillium purpurogenum*; *Rhizopus* species, such as, for example, *Rhizopus stolonifer*; *Sclerotinia* species, such as, for example, *Sclerotinia sclerotiorum*; *Verticilium* species, such as, for example, *Verticilium alboatrum*;

Seed- and soil-borne rot and wilt diseases, and also diseases of seedlings, caused, for example, by *Alternaria* species, such as, for example, *Alternaria brassicicola*; *Aphanomyces* species, such as, for example, *Aphanomyces euteiches*; *Ascochyta* species, such as, for example, *Ascochyta lentis*; *Aspergillus* species, such as, for example, *Aspergillus flavus*; *Cladosporium* species, such as, for example, *Cladosporium herbarum*; *Cochliobolus* species, such as, for example, *Cochliobolus sativus* (conidiaform: *Drechslera, bipolaris* syn: *Helminthosporium*); *Colletotrichum* species, such as, for example, *Colletotrichum coccodes*; *Fusarium* species, such as, for example, *Fusarium culmorum*; *Gibberella* species, such as, for example, *Gibberella zeae*; *Macrophomina* species, such as, for example, *Macrophomina phaseolina*; *Microdochium* species, such as, for example, *Microdochium nivale*; *Monographella* species, such as, for example, *Monographella nivalis*; *Penicillium* species, such as, for example, *Penicillium expansum*; *Phoma* species, such as, for example, *Phoma lingam*; *Phomopsis* species, such as, for example, *Phomopsis sojae*; *Phytophthora* species, such as, for example, *Phytophthora cactorum*; *Pyrenophora* species, such as, for example, *Pyrenophora graminea*; *Pyricularia* species, such as, for example, *Pyricularia oryzae Pythium* species, such as, for example, *Pythium ultimum*; *Rhizoctonia* species, such as, for example, *Rhizoctonia solani*; *Rhizopus* species, such as, for example, *Rhizopus oryzae*; *Sclerotium* species, such as, for example, *Sclerotium rolfsii*; *Septoria* species, such as, for example, *Septoria nodorum*; *Typhula* species, such as, for example, *Typhula incarnate*; *Verticillium* species, such as, for example, *Verticillium dahliae*;

Cancerous diseases, galls and witches' broom caused, for example, by *Nectria* species, such as, for example, *Nectria galligena*;

Wilt diseases caused, for example, by *Monilinia* species, such as, for example, *Monilinia laxa*;

Deformations of leaves, flowers and fruits caused, for example, by *Exobasidium* species, such as, for example, *exobasidium vexans*; *Taphrina* species, such as, for example, *Taphrina deformans*;

Degenerative diseases of woody plants caused, for example, by *Esca* species, such as, for example, *Phaemoniella clamydospora* and *Phaeoacremonium aleophilum* and *Fomitiporia mediterranea*; *Ganoderma* species, such as, for example, *Ganoderma boninense*; *Rigidoporus* species, such as, for example, *Rigidoporus lignosus*;

Club root diseases caused, for example, by *Plasmodiophora* species, such as, for example, *Plasmodiophora brassicae*;

Diseases of flowers and seeds caused, for example, by *Botrytis* species, such as, for example, *Botrytis cinerea*;

Diseases of plant tubers caused, for example, by *Rhizoctonia* species, such as, for example, *Rhizoctonia solani*; *Helminthosporium* species, such as, for example, *Helminthosporium solani*;

Diseases caused by bacteriopathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soy beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

In addition, the compound of formula (I) in combination with at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant as given herein can also exhibit very good antimycotic activity, in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi by no means limits the mycotic spectrum which can be covered, but is only for illustration.

Furthermore, the compound of formula (I) in combination with at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant as given herein can also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxins, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudo graminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

Moreover, plants and plant parts which are mentioned herein are all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

As has already been mentioned above, all plants and their parts may be treated in accordance with the invention. In a preferred embodiment, plant species and plant varieties, and their parts, which grow wild or which are obtained by traditional biological breeding methods such as hybridization or protoplast fusion are treated. In a further preferred embodiment, transgenic plants and plant varieties which have been obtained by recombinant methods, if appropriate in combination with traditional methods (genetically modified organisms), and their parts are treated. The term "parts" or "parts of plants" or "plant parts" has been explained hereinabove. Plants of the plant varieties which are in each case commercially available or in use are especially preferably treated in accordance with the invention. Plant varieties are understood as meaning plants with novel traits which have been bred both by traditional breeding, by mutagenesis or by recombinant DNA techniques. They may take the form of varieties, races, biotypes and genotypes.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved with by using or employing the compound of formula (I), preferably compound (I-1-1), (I-1-2), as well as the mixtures (I-1-1)/(I-1-7), (I-1-2)/(I-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant, include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; *Lauraceae*, for example avocado, Cinnamomum, camphor, or else plants such as tobacco, nuts, coffee, aubergine, sugar cane, tea, pepper, grapevines, hops, bananas, latex plants and ornamentals, for example flowers, shrubs, deciduous trees and coniferous trees.

The following plants are considered to be particularly suitable target crops for using or employing the compound of formula (I), preferably compound (I-1-1), (I-1-2), as well as the mixtures (I-1-1)/(1-1-7), (1-1-2)/(1-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees are: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus*: *A. hippocastanum, A. pariflora, A. carnea*; from the tree species *Platanus*: *P. aceriflora, P. occidentalis, P. racemosa*; from the tree species *Picea*: *P. abies*; from the tree species *Pinus*: *P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobus*; from the tree species *Eucalyptus*: *E. grandis, E. globulus, E. camadentis, E. nitens, E. obliqua, E. regnans, E. pilularus*.

Especially preferred trees which can be improved in accordance with the method according to the invention are: from the tree species *Pinus*: *P. radiata, P. ponderosa, P. contorta, P. sylvestre, P. strobus*; from the tree species *Eucalyptus*: *E. grandis, E. globulus, E. camadentis*.

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha Gaudin*), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.); fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam), tall fescue (*Festuca arundinacea* Schreb.) and meadow fescue (*Festuca elanor* L.); ryegrasses (*Lolium* spp.), such as annual ryegrass (*Lolium multiflorum* Lam), perennial ryegrass (*Lolium perenne* L.) and Italian ryegrass (*Lolium multiflorum* Lam); and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turf grasses are Bermuda grass (*Cynodon* spp. L. C. Rich), zoysia grass (*Zoysia* spp. Willd.), St. Augustine grass (*Stenotaphrum secundatum* Walt Kuntze), centipede grass (Eremochloa ophiuroides Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), blue grama (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turf grasses are generally preferred for the use according to the invention. Especially preferred are bluegrass, benchgrass and redtop, fescues and ryegrasses. Bentgrass is especially preferred.

It is understood that if not mentioned otherwise all references to plant, plant parts, seeds, plants emerging from the seed includes conventional or transgenic plant, plant parts, seeds, plants emerging from the seed. Transgenic (genetically modified) plants are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), using or employing the compound of formula (I), preferably compound (I-1-1), (I-1-2), as well as the mixtures (I-1-1)/(1-1-7), (1-1-2)/(1-1-8) and the at least one biological control agent selected from bacteria, in particular spore-forming bacteria, fungi or yeasts, protozoas, viruses, entomopathogenic nematodes and botanical extracts, or products produced by microorganisms including proteins or secondary metabolites, and optionally the inoculant the treatment according to the invention may also result in super-additive ("synergistic") effects. Thus, for example, by using or employing the compound of formula (I), preferably compound (I-1-1), (I-1-2), as well as the mixtures (I-1-1)/(1-1-7), (1-1-2)/(1-1-8) and the at least one biological control agent selected from bacteria, in particular spore-forming bacteria, fungi or yeasts, protozoas, viruses, entomopathogenic nematodes, and botanical extracts, or a protein produced by bacteria, and optionally the inoculant in the treatment according to the invention, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the compound of formula (I), preferably compound (I-1-1), (I-1-2), as well as the mixtures (I-1-1)/(1-1-7), (1-1-2)/(1-1-8) and the at least one biological control agent selected from bacteria, in particular spore-forming bacteria, fungi or yeasts, protozoas, viruses, entomopathogenic nematodes, and botanical extracts, or products produced by microorganisms including proteins or secondary metabolites, and optionally the inoculant in the treatment according to the invention may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses, Thus, by using or employing the compound of formula (I), preferably compound (I-1-1), (I-1-2), as well as the mixtures (I-1-1)/(1-1-7), (1-1-2)/(1-1-8) and the at least one biological control agent selected from bacteria, in particular spore-forming bacteria, fungi or yeasts, protozoas, viruses, entomopathogenic nematodes, and botanical extracts or products produced by microorganisms including proteins or secondary metabolites, and optionally the inoculant in the treatment according to the invention, plants can be protected against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from Streptomyces species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712). The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) An insecticidal crystal protein from Bacillus thuringiensis or an insecticidal portion thereof, such as the insecticidal crystal proteins listed online at:
http://www.lifesci.sussex.ac.uk/Home/Neil_Crickmore/Bt/, or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141_and WO 2007/107302), or such proteins encoded by synthetic genes as e.g. described in U.S. patent application Ser. No. 12/249,016; or 2) a crystal protein from Bacillus thuringiensis or a portion thereof which is insecticidal in the presence of a second other crystal protein from Bacillus thuringiensis or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from Bacillus thuringiensis, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from Bacillus thuringiensis or Bacillus cereus, or an insecticidal portion thereof, such as the vegetative insecticidal (VIP) proteins listed at:
http://www.lifesci.sussex.ac.uk/home/Neil_Crickmore/Bt/vip.html, e.g. proteins from the VIP3Aa protein class; or 6) secreted protein from Bacillus thuringiensis or Bacillus cereus which is insecticidal in the presence of a second secreted protein from Bacillus thuringiensis or B. cereus, such as the binary toxin made up of the VIP1A and VIP2A proteins (WO 94/21795); or 7) hybrid insecticidal protein comprising parts from different secreted proteins from Bacillus thuringiensis or Bacillus cereus, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose) polymerase (PARP) gene in the plant cells or plants b. plants which contain a stress tolerance enhancing transgene capable of reducing the expression and/or the activity of the poly(ADP-ribose)glycohydrolase (PARG) encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1, 4-glucans, plants producing alternan, 3) transgenic plants which produce hyaluronan.

4) transgenic plants or hybrid plants, such as onions with characteristics such as 'high soluble solids content', low pungency' (LP) and/or 'long storage' (LS).

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes, b) Plants, such as cotton plants, containing an altered form of rsw2 or rsw3 homologous nucleic acids, c) Plants, such as cotton plants, with increased expression of sucrose phosphate synthase, d) Plants, such as cotton plants, with increased expression of sucrose synthase, e) Plants, such as cotton plants, wherein the timing of the plasmodesmatal gating at the basis of the fiber cell is altered, e.g. through downregulation of fiberselective β 1,3-glucanase, f) Plants, such as cotton plants, having fibers with altered reactivity, e.g. through the expression of N-acteylglucosaminetransferase gene including nodC and chitin-synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content, b) Plants such as oilseed rape plants, producing oil having a low linolenic acid content, c) Plant such as oilseed rape plants, producing oil having a low level of saturated fatty acids.

Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the $N_t$-Inhh, IIR-INV gene) or which possess a dwarf phenotype (Gene A-20 oxidase).

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS (tolerance to sulphonylureas, for example maize) Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

The invention is illustrated by the following examples without restricting the scope of invention:

Formula for the Efficacy of the Combination of Two Compounds

The expected efficacy of a given combination of two compounds is calculated as follows (see Colby, S. R., "Calculating Synergistic and antagonistic Responses of Herbicide Combinations", Weeds 15, pp. 20-22, 1967):

if
X is the efficacy expressed in % mortality of the untreated control for test compound A at a concentration of m ppm or m g/ha,
Y is the efficacy expressed in % mortality of the untreated control for test compound B at a concentration of n ppm or n g/ha,
E is the efficacy expressed in % mortality of the untreated control using the mixture of A and B at m and n ppm or m and n g/ha,
then is $$E = X + Y - \frac{X \cdot Y}{100}.$$

If the observed insecticidal efficacy of the combination is higher than the one calculated as "E", then the combination of the two compounds is more than additive, i.e., there is a synergistic effect.

Example 1

*Phaedon cochleariae* Larvae—Spray Application

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. The preparation of bacteria, fungi or yeast products contains $10^9$-$10^{10}$ spores/g or cells/g, the preparation of the virus $10^{13}$ particles/l. To produce a suitable preparation of a biological suspension the cells, viruses or spores are diluted with emulsifier-containing water to the desired concentration.

Chinese cabbage (*Brassica pekinensis*) leaf-discs are sprayed with a preparation of the active ingredient of the desired concentration. Once dry, the leaf discs are infested with mustard beetle larvae (*Phaedon cochleariae*).

After the specified period of time, mortality in % is determined. 100% means that all the beetle larvae have been killed; 0% means that none of the beetle larvae have been killed. The mortality values thus determined are recalculated using the Colby-formula.

The following combinations of compound and biological showed a synergistic effect according to the invention:

TABLE 1

| *Phaedon cochleariae* larvae - Test | | |
| --- | --- | --- |
| Active ingredient/biological control agent | Concentration g ai/ha | Mortality in % after $2^d$ |
| Compound (I-1-1/I-1-7) | 0.8 | 67 |
| Thymol | 1000 | 0 |
| | | obs.* cal.** |
| Compound (I-1-1/I-1-7) + Thymol | 0.8 + 1000 | 100    67 |
| Active ingredient/biological control agent | Concentration g ai/ha | Mortality in % after $6^d$ |
| Compound (I-1-1/I-1-7) | 0.8 | 83 |
| | 0.16 | 67 |
| *Bacillus amyloliquefaciens* strain FZB 42 (Rhizovital flüssig, 2.5 × $10^{10}$ cfu/ml) | 2000 | 0 |
| | | obs.* cal.** |
| Compound (I-1-1/I-1-7) + *Bacillus amyloliquefaciens* | 0.8 + 2000 | 100    83 |
| *Metschnikowia fructicola* (Shemer, 2 × $10^{10}$ cells/g) | 1000 | 0 |
| | | obs.* cal.** |
| Compound (I-1-1/I-1-7) + *M. fructicola* | 0.8 + 1000 | 100    83 |
| *Cydia pomonella* Granulosis virus (CpGV) (MiniMadex) | 1000 | 0 |
| | | obs.* cal.** |
| Compound (I-1-1/I-1-7) + CpGV Virus | 0.8 + 1000 | 100    83 |
| *Metarhizium anisopliae* (MET52, 9 × $10^8$ cfu/g) | 100 | 0 |
| Compound (I-1-1/I-1-7) + *M. anisopliae* | | obs.* cal.** |
| | 0.8 + 100 | 100    83 |
| *Paecilomyces lilacinus* strain 251 (BioAct, 1 × $10^{10}$ spores/g) | 4000 | 0 |
| Compound (I-1-1/I-1-7) + *Paecilomyces* | | obs.* cal.** |
| *lilacinus* strain 251 | 0.16 + 4000 | 100    67 |

*obs. = observed insecticidal efficacy,
**cal. = efficacy calculated with Colby-formula Example 2

*Spodoptera frugiperda*—Spray Application

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. The preparation of the bacteria, fungi or yeast products contains $10^9$-$10^{10}$ spores/g or cells/g, the preparation of the virus $10^{13}$ particles/l. To produce a suitable preparation of a biological suspension the cells, viruses or spores are diluted with emulsifier-containing water to the desired concentration.

Corn (*Zea mais*) leaf-discs are sprayed with a preparation of the active ingredient of the desired concentration. Once dry, the leaf discs are infested with fall armyworm larvae (*Spodoptera frugiperda*).

After the specified period of time, mortality in % is determined. 100% means that all the caterpillars have been killed; 0% means that none of the caterpillars have been killed. The mortality values thus determined are recalculated using the Colby-formula.

The following combinations of compound and biological showed a synergistic effect according to the invention:

TABLE 2

*Spodoptera frugiperda* - Test

| Active ingredient/biological control agent | Concentration g ai/ha | Mortality in % after $2^d$ | |
|---|---|---|---|
| Compound (I-1-1/I-1-7) | 0.16 | 0 | |
| *Paecilomyces lilacinus* strain 251 (BioAct, 1 × $10^{10}$ spores/g) | 4000 | 0 | |
| | | obs.* | cal.** |
| Compound (I-1-1/I-1-7) + *Paecilomyces lilacinus* strain 251 | 0.16 + 4000 | 100 | 0 |
| Harpin | 1.5 | 0 | |
| | | obs.* | cal.** |
| Compound (I-1-1/I-1-7) + Harpin | 0.16 + 1.5 | 50 | 0 |

| Active ingredient/biological control agent | Concentration g ai/ha | Mortalility in % after $6^d$ | |
|---|---|---|---|
| Compound (I-1-1/I-1-7) | 0.16 | 67 | |
| *Cydia pomonella* Granulosis virus (CpGV) (MiniMadex) | 1000 | 0 | |
| | | obs.* | cal.** |
| Compound (I-1-1/I-1-7) + CpGV Virus | 0.16 + 1000 | 83 | 67 |

*obs. = observed insecticidal efficacy,
**cal. = efficacy calculated with Colby-formula Example 3

*Tetranychus-urticae*—Test (OP-Resistant Spray Application)

Solvent: 78 parts by weight acetone
1.5 parts by weight dimethylformamide
Wetting agent: 0.5 parts by weight alkylarylpolyglcolether
To produce a suitable preparation of active compound, 1 part by weight of active compound is mixed with the stated amount of solvent and emulsifier, and the concentrate is diluted with emulsifier-containing water to the desired concentration. The preparation of the bacteria, fungi or yeast products contains $10^9$-$10^{10}$ spores/g or cells/g. To produce a suitable preparation of a biological suspension the cells, viruses or spores are diluted with emulsifier-containing water to the desired concentration.

French beans (*Phaseolus vulgaris*) infected with all developmental stages of the two spotted spider mite (*Tetranychus urticae*), are sprayed with a preparation of the active ingredient at the desired dose rates.

After the specified period of time, activity in % is determined Thus 100% means that all spider mites have been killed and 0% means that none of the spider mites have been killed. The mortality values determined thus are recalculated using the Colby-formula (see sheet 1).

The following combinations of compound and biological showed a synergistic effect according to the invention:

TABLE 3

*Tetranychus urticae* - Test

| Active ingredient/biological control agent | Concentration g ai/ha | Mortality in % after $6^d$ | |
|---|---|---|---|
| Compound (I-1-1/I-1-7) | 4 | 0 | |
| | 0.8 | 0 | |
| Harpin | 1.5 | 0 | |
| | | obs.* | cal.** |
| Compound (I-1-1/I-1-7) + Harpin | 4 + 1.5 | 70 | 0 |
| *Metschnikowia fructicola* (Shemer, 2 × $10^{10}$ cells/g) | 1000 | 0 | |
| | | obs.* | cal.** |
| Compound (I-1-1/I-1-7) + *M. fructicola* | 0.8 + 1000 | 100 | 0 |

*obs. = observed insecticidal efficacy,
**cal. = efficacy calculated with Colby-formula Example 4

Seed Treatment—Germination Test Soybean

Seeds of soybean (*Glycine max*) were treated by being mixed with the desired amount of active compound and spores and water. After drying, 25 seeds were sown into each pot filled with sandy loam.

After the specified period of time the level of activity expressed in % was determined. The level of activity was calculated on the basis of the number of soybean plants which have successfully germinated.

The following combination of compound and biological showed a superior germination effect compared to the single treatments and control:

TABLE 4

Germination of Soybean

| Active ingredient/biological control agent | Concentration g ai/kg seeds | % Germination after 4 days control was set 100% |
|---|---|---|
| Control (seeds without treatment) | | 100 |
| Compound (I-1-1/I-1-7) | 0.3 | 92.98 |
| | 0.15 | 92.98 |
| *Bacillus subtilis* strain GB 03 Kodiak, 5.5 × $10^{10}$ spores/g) | 0.156 | 84.21 |
| | 0.078 | 77.19 |
| Compound (I-1-1/I-1-7) + *Bacillus subtilis* | 0.15 + 0.156 | 107.02 |
| | 0.3 + 0.078 | 110.53 |

| Active ingredient/biological control agent | Concentration g ai/kg seeds | % Germination after 5 days control was set 100% |
|---|---|---|
| Control (seeds without treatment) | | 100 |
| Compound (I-1-1/I-1-7) | 0.15 | 96.55 |
| *Bacillus amyloliquefaciens* FZB 42 (Rhizovital flüssig, 2.5 × $10^{10}$ cfu/ml) | 0.15 | 91.38 |
| Compound (I-1-1/I-1-7) + *Bacillus amyloliquefaciens* | 0.15 + 0.15 | 100 |

Example 5

*Phaedon cochleariae* Larvae—Spray Application

Solvent: 78.0 parts by weight of acetone 1.5 parts by weight of dimethylformamide Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. To produce a suitable preparation of a biological suspension the cells, viruses or spores are diluted with emulsifier-containing water to the desired concentration.

Chinese cabbage (*Brassica pekinensis*) leaf-discs are sprayed with a preparation of the active ingredient of the desired concentration. Once dry, the leaf discs are infested with mustard beetle larvae (*Phaedon cochleariae*).

After the specified period of time, mortality in % is determined. 100% means that all the beetle larvae have been killed; 0% means that none of the beetle larvae have been killed. The mortality values thus determined are recalculated using the Colby-formula.

The following combinations of compound and biological showed a synergistic effect according to the invention:

TABLE 5

| *Phaedon cochleariae* larvae - Test | | | |
|---|---|---|---|
| Active ingredient/biological control agent | Concentration ppm | Mortality in % after $1^d$ | |
| Compound (I-1-1/I-1-7) | 0.8 | 35 | |
| *Bacillus pumilus* strain QST2808 (Sonata, $1.0 \times 10^9$ cfu/g) | 1000 | 0 | |
| | | obs.* | cal.** |
| Compound (I-1-1/I-1-7) + *Bacillus pumilus* strain QST2808 1:1250 | 0.8 + 1000 | 60 | 35 |

*obs. = observed insecticidal efficacy,

**cal. = efficacy calculated with Colby-formula

The invention claimed is:

1. A composition comprising an anthranilic acid diamide derivative with one or more heteroaromatic and heterocyclic substituents of formula (I)

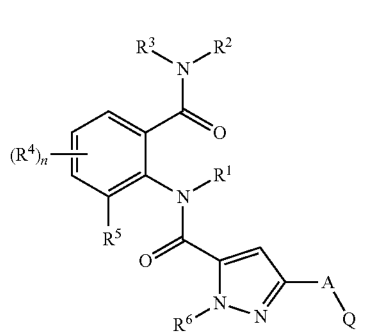

(I)

in which $R^1$ represents hydrogen, amino or hydroxyl or represents $C_1$-$C_6$-alkyl, $C_2$-$C_6$-alkenyl, $C_2$-$C_6$-alkynyl or $C_3$-$C_6$-cycloalkyl each of which is unsubstituted or substituted one or more times by identical or different substituents selectable independently of one another from halogen, cyano, nitro, hydroxyl, $C_1$-$C_4$-alkoxy, $C_1$-$C_4$-alkylthio, $C_1$-$C_4$-alkylsulphonyl, ($C_1$-$C_4$-alkoxy)carbonyl, $C_1$-$C_4$-alkylamino, di($C_1$-$C_4$-alkyl)amino, $C_3$-$C_6$-cycloalkylamino or ($C_1$-$C_4$-alkyl)$C_3$-$C_6$-cycloalkylamino, $R^2$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkylamino, di($C_1$-$C_4$-alkyl)amino, $C_3$-$C_6$-cycloalkylamino, $C_2$-$C_6$-alkoxycarbonyl or $C_2$-$C_6$-alkylcarbonyl, $R^3$ represents hydrogen or represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from halogen, cyano, nitro, hydroxyl, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl or $C_3$-$C_6$-trialkylsilyl, $R^3$ further represents $C_1$-$C_6$-alkyl, $C_1$-$C_6$-alkoxy, $C_2$-$C_6$-alkenyl, $C_2$-$C_6$-alkynyl each of which is optionally substituted one or more times by identical or different substituents selectable independently of one another from amino, $C_3$-$C_6$-cycloalkylamino or a 5- or 6-membered heteroaromatic ring, $R^3$ likewise further represents $C_3$-$C_{12}$-cycloalkyl, $C_3$-$C_{12}$-cycloalkyl-$C_1$-$C_6$-alkyl and $C_4$-$C_{12}$-bicycloalkyl, the substituents being selectable independently of one another from halogen, cyano, nitro, hydroxyl, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-alkylsulphimino, $C_1$-$C_4$-alkylsulphimino-$C_1$-$C_4$-alkyl, $C_1$-$C_4$-alkylsulphimino-$C_2$-$C_5$-alkylcarbonyl, $C_1$-$C_4$-alkylsulphoximino, $C_1$-$C_4$-alkylsulphoximino-$C_1$-$C_4$-alkyl, $C_1$-$C_4$-alkylsulphoximino-$C_2$-$C_5$-alkylcarbonyl, $C_2$-$C_6$-alkoxycarbonyl, $C_2$-$C_6$-alkylcarbonyl, $C_3$-$C_6$-trialkylsilyl or a 5- or 6-membered heteroaromatic ring, $R^2$ and $R^3$ can be joined to one another via two to six carbon atoms and form a ring which where appropriate additionally contains a further nitrogen, sulphur or oxygen atom and where appropriate may be substituted one to four times by $C_1$-$C_2$-alkyl, halogen, cyano, amino or $C_1$-$C_2$-alkoxy, $R^2$ and $R^3$ further together represent $=S(C_1$-$C_4$-alkyl$)_2$ or $=S(O)(C_1$-$C_4$-alkyl$)_2$, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl)($C_1$-$C_4$-alkoxy)imino or $C_3$-$C_6$-trialkylsilyl, or two $R^4$s, via adjacent carbon atoms, form a ring which represents $-(CH_2)_3-$, $-(CH_2)_4-$, $-(CH_2)_5-$, $-(CH{=}CH-)_2-$, $-OCH_2O-$, $-O(CH_2)_2O-$, $-OCF_2O-$, $-(CF_2)_2O-$, $-O(CF_2)_2O-$, $-(CH{=}CH-CH{=}N)-$ or $-(CH{=}CH-N{=}CH)-$, two $R^4$s further, via adjacent carbon atoms, form the following fused rings, which where appropriate are substituted one or more times by identical or different substituents selectable independently of one another from hydrogen, $C_1$-$C_6$-alkyl, $C_3$-$C_6$-cycloalkyl, $C_1$-$C_6$-haloalkyl, $C_3$-$C_6$-halocycloalkyl, halogen, $C_1$-$C_6$-alkoxy, $C_1$-$C_4$-alkylthio($C_1$-$C_6$-alkyl), $C_1$-$C_4$-alkylsulphinyl($C_1$-$C_6$-alkyl), $C_1$-$C_4$-alkylsulphonyl($C_1$-$C_6$-alkyl), $C_1$-$C_4$-alkylamino, di($C_1$-$C_4$-alkyl)amino or $C_3$-$C_6$-cycloalkylamino,

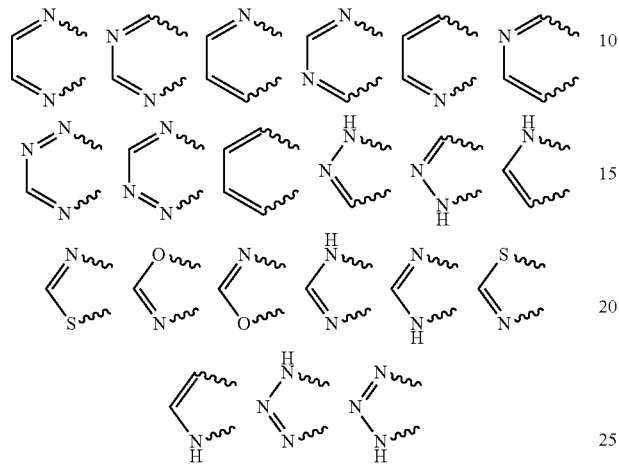

n represents 0 to 3, $R^5$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro or $C_3$-$C_6$-trialkylsilyl, $R^6$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl or

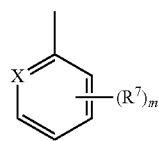

$R^6$ further represents $C_3$-$C_6$-cycloalkoxy, $R^7$ represents independently at each occurrence hydrogen, $C_1$-$C_6$-alkyl, $C_3$-$C_6$-cycloalkyl, $C_1$-$C_6$-haloalkyl, halogen, cyano, nitro, $C_1$-$C_4$-alkoxy, $C_1$-$C_4$-haloalkoxy, $C_1$-$C_4$-alkylthio or $C_1$-$C_4$-haloalkylthio, m represents 0 to 4, X represents N, CH, CF, CCl, CBr or CI, A represents —$CH_2$—, —$CH_2O$—, —$CH_2OCH_2$—, —$CH_2S$—, —$CH_2SCH_2$—, —$CH_2N(C_1$-$C_6$-alkyl)-, —$CH_2N(C_1$-$C_6$-alkyl)CH_2$—, —$CH[CO_2(C_1$-$C_6$-alkyl)]-, —CH(CN)—, —CH($C_1$-$C_6$-alkyl)-, —C(di-$C_1$-$C_6$-alkyl)-, —$CH_2CH_2$— or —C=NO($C_1$-$C_6$-alkyl)-, Q represents a 5- or 6-membered heteroatomatic ring or an aromatic 8-, 9- or 10-membered fused heterobicyclic ring system, the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, Q further represents a 5- or 6-membered heteroaromatic or heterocyclic ring or an aromatic 8-, 9- or 10-membered fused heterobicyclic ring system, the ring or the ring system being unsubstituted or substituted one or more times by identical or different substituents selectable independently of one another from hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $CO_2H$, $CO_2NH_2$, $NO_2$, OH, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, di($C_1$-$C_4$-alkyl)amino, $C_3$-$C_6$-cycloalkylamino, ($C_1$-$C_6$-alkyl)carbonyl, ($C_1$-$C_6$-alkoxy)carbonyl, ($C_1$-$C_6$-alkyl)aminocarbonyl, di($C_1$-$C_4$-alkyl)aminocarbonyl, tri($C_1$-$C_2$-alkyl)silyl and ($C_1$-$C_4$-alkyl)($C_1$-$C_4$-alkoxy)imino, or the substituents being selectable independently of one another from phenyl or a 5- or 6-membered heteroaromatic ring, it being possible for phenyl or the ring to be unsubstituted or substituted one or more times by identical or different $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, OH, $C_1$-$C_4$-alkoxy, $C_1$-$C_4$-haloalkoxy substituents, and/or the compound of formula (I) also comprises an N-oxide and/or salt thereof, and at least one biological control agent selected from Thymol, *Bacillus amyloliquefaciens* strain FZB 42, *Metschnikowiafructicola*, *Cydiapomonella granulosis* virus, *Metarhiziumanisopliae*, *Paecilomyceslilacinus* strain 251, Harpin protein, *Bacillus subtilis* strain GB 03, and *Bacillus pumilus* strain QST2808, and optionally an inoculant, said composition being capable of being used for reducing overall damage of one or more plants and/or plant parts and/or losses in one or more of harvested fruits or vegetables caused by one or more of insects, nematodes and phytopathogens.

2. A composition according to claim 1 wherein the anthranilic acid diamide derivative is a compound of formula (I-1)

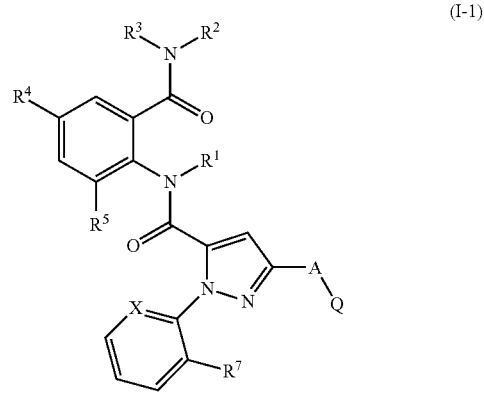

and/or a N-oxide and/or salt thereof.

3. The composition according to claim 1, wherein the inoculant is present and is selected from the group consisting of bacteria of the genus *Rhizobium leguminosarum, Rhizobium tropici, Rhizobium loti, Rhizobium trifolii, Rhizobium meliloti, Rhizobium fredii, Azorhizobium caulinodans, Pseudomonas, Azospirillum, Azotobacter, Streptomyces, Burkholdia, Agrobacterium*, Endo-, Ecto-, Vesicular-*Arbuscular Mycorhizza*.

4. A method for reducing overall damage of one or more plants and/or plant parts and/or losses in one or more of harvested fruits or vegetables caused by one or more insects and/or phytopathogens comprising simultaneously or sequentially applying a composition comprising compound of formula (I) and/or N-oxide or salt thereof as defined in claim 1 and at least one biological control agent selected from the group consisting of bacteria, fungi or yeasts, protozoas, viruses, entomopathogenic nematodes and botanical extracts, or products produced by microorganisms including proteins or secondary metabolites, and optionally at least an inoculant on the plant, plant parts, harvested fruits or vegetables.

5. The method according to claim 4 wherein the applying is to a plant part which is a seed or a plant emerging from the seed.

6. The method according to claim 5, wherein the seed is from a conventional or a transgenic plant.

7. The method according to claim 4, wherein the plant is a horticultural crop selected from the group consisting of carrots, pumpkin, squash, zucchini, potato, sweet corn, onions, ornamentals, medicinal herbs, culinary herbs, tomatoes, spinach, pepper, melon, lettuce, cucumber, celery, beets, cabbage, cauliflower, broccoli, Brussels sprouts, kohlrabi, kale, radish, rutabaga, turnip, asparagus, bean, pea, apples, raspberry, strawberry, banana, mango, grapes, peaches, pears, guava, pineapple, pomegranate, garlic, capsicum, chilli, radish, star fruit, tapioca, walnuts, lemon, mandarin, mangold, mushroom, olive, orange, papaya, paprika, passion fruit, peanuts, pecan nuts, prune, pistachio nuts, persimmon, pamplemouse (grapefruit), eggplant, endive, cranberry, gooseberry, hazel nuts, kiwifruit, almonds, amaranth, apricot, artichoke, avocado, blackberry, cashew nut, cherry, clementine, coconut, and cantaloupes.

8. The method according to claim 4, wherein the plant is a broad acre crop selected from the group consisting of cotton, corn, soybean, cereals, canola, oil seed rape, sugar cane and rice.

9. A composition according to claim 1, comprising a compound of formula (I-1-1)

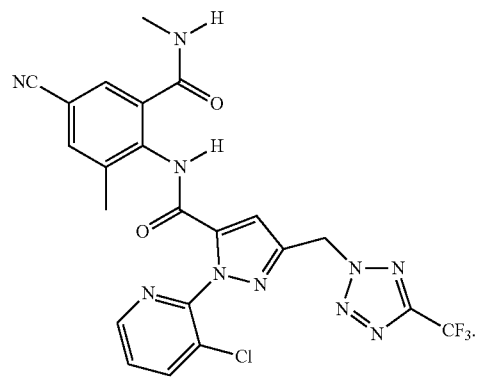

(I-1-1)

10. A composition according to claim 9, further comprising another compound of formula (I) other than (I-1-1).

11. A composition according to claim 9, wherein the biological control agent comprises Thymol.

12. A composition according to claim 9, wherein the biological control agent comprises *Bacillus amyloliuefaciens* strain FZB 42.

13. A composition according to claim 9, wherein the biological control agent comprises *Metschnikowiafructicola*.

14. A composition according to claim 9, wherein the biological control agent comprises *Cydiapomonella granulosis* virus.

15. A composition according to claim 9, wherein the biological control agent comprises *Metarhiziumanisopliae*.

16. A composition according to claim 9, wherein the biological control agent comprises *Paecilomyceslilacinus* strain 251.

17. A composition according to claim 9, wherein the biological control agent comprises Harpin protein.

18. A composition according to claim 9, comprising 0.1 to 80% by weight of compounds of formula (I) and 2 to 80% by weight of the biological control agent.

19. A composition according to claim 9, wherein the biological control agent comprises *Bacillus subtilis* strain GB 03.

20. A composition according to claim 10, wherein the compounds of formula (I) and the biological control agent act synergistically.

21. A composition according to claim 9, wherein the biological control agent comprises *Bacillus pumilus* strain QST2808.

* * * * *